United States Patent [19]  [11] 4,229,460
Heeres et al.  [45] Oct. 21, 1980

[54] HETEROCYCLIC DERIVATIVES OF 1-(1,3-DIOXOLAN-2-YLMETHYL)-1H-1,2,4-TRIAZOLES HAVING ANTIFUNGAL AND ANTIBACTERIAL PROPERTIES

[75] Inventors: Jan Heeres, Vosselaar; Leo J. J. Backx, Arendonk; Joseph H. Mostmans, Antwerp, all of Belgium

[73] Assignee: Janssen Pharmaceutica N.V., Beerse, Belgium

[21] Appl. No.: 50,371

[22] Filed: Jun. 20, 1979

Related U.S. Application Data

[60] Division of Ser. No. 853,726, Nov. 21, 1977, Pat. No. 4,160,841, which is a continuation-in-part of Ser. No. 764,265, Jan. 31, 1977, abandoned.

[51] Int. Cl.$^2$ .......................... A01N 9/22; A01N 9/12; C07D 407/14

[52] U.S. Cl. .................................. 424/269; 424/232; 548/251; 548/252; 548/262; 548/265

[58] Field of Search ................. 424/269; 548/262, 265

[56] References Cited

U.S. PATENT DOCUMENTS 4,160,838   7/1979   Van Reet et al. .................... 424/269

FOREIGN PATENT DOCUMENTS 2804096   8/1978   Fed. Rep. of Germany .......... 424/269

*Primary Examiner*—Alton D. Rollins
*Attorney, Agent, or Firm*—Salvatore R. Conte

[57] ABSTRACT

Heterocyclic derivatives of 1-(1,3-dioxolan-2-ylmethyl)-1H-1,2,4-triazoles useful as antifungal and antibacterial agents.

3 Claims, No Drawings

HETEROCYCLIC DERIVATIVES OF 1-(1,3-DIOXOLAN-2-YLMETHYL)-1H-1,2,4-TRIAZOLES HAVING ANTIFUNGAL AND ANTIBACTERIAL PROPERTIES

CROSS-REFERENCE TO RELATED APPLICATIONS

This is a divisional of our co-pending application, Ser. No. 853,726, filed Nov. 21, 1977, now U.S. Pat. No. 4,160,841 which in turn is a continuation-in-part of application, Ser. No. 764,265, filed Jan. 31, 1977, now abandoned.

BACKGROUND OF THE INVENTION

In U.S. Pat. Nos. 3,575,999, 3,936,470 and Belg. Pat. No. 835,579 there are described a number of 1-(1,3-dioxolan-2-yl-methyl)-1H-imidazoles and 1H-1,2,4-triazoles having antifungal and antibacterial properties. The compounds of this invention differ from the foregoing essentially by the nature of the complex substituent group present in the 4-position of the dioxolane moiety.

DESCRIPTION OF THE PREFERRED EMBODIMENTS

This invention is concerned with novel 1H-imidazole and 1H-1,2,4-triazole derivatives which may structurally be represented by the formula:

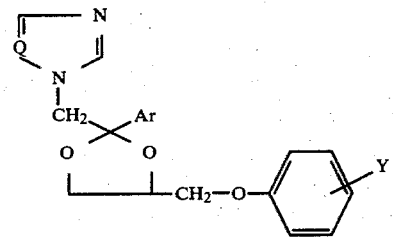

(I)

and the pharmaceutically acceptable acid addition salts and stereo-chemically isomeric forms thereof, wherein:
  Q is a member selected from the group consisting of CH and N;
  Ar is a member selected from the group consisting of phenyl and substituted phenyl, said substituted phenyl having from 1 to 3 substituents independently selected from the group consisting of halo, lower alkyl and lower alkyloxy; and
  the radical Y is a member selected from the group consisting of:
    a 1H-pyrrol-1-yl radical of the formula

(a);

a 1H-pyrazol-1-yl radical of the formula

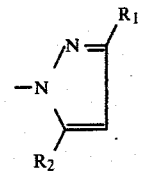

(b)

wherein $R_1$ is selected from the group consisting of hydrogen, lower alkyl, lower alkylthio and phenyl, and, $R_2$ is selected from the group consisting of hydrogen, lower alkyl and phenyl;
a 1H-imidazol-1-yl radical of the formula

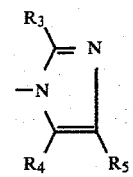

(c)

wherein $R_3$ is selected from the group consisting of hydrogen, lower alkyl, phenyl, lower alkylthio, lower alkylsulfinyl and lower alkylsulfonyl, $R_4$ is selected from the group consisting of hydrogen, lower alkyl and phenyl, and, $R_5$ is selected from the group consisting of hydrogen and phenyl;
a 1H-1,2,4-triazol-1-yl radical of the formula

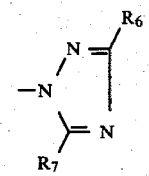

(d)

wherein $R_2$ is selected from the group consisting of hydrogen and lower alkylthio, and, $R_7$ is selected from the group consisting of hydrogen, lower alkyl and phenyl;
a 4H-1,2,4-triazol-4-yl radical of the formula

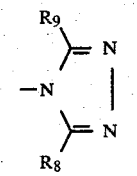

(e)

wherein $R_8$ is selected from the group consisting of hydrogen, lower alkyl, lower alkyloxy, lower alkylthio, lower alkylsulfinyl and lower alkylsulfonyl, and, $R_9$ is selected from the group consisting of hydrogen and lower alkyl;
a 2,3-dihydro-4H-1,2,4-triazol-4-yl radical of the formula

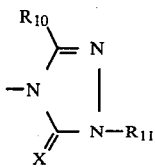  (f)

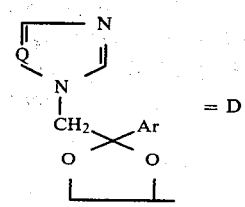 = D

Q is CH or N.

wherein X is selected from the group consisting of O and S, and, $R_{10}$ and $R_{11}$ are each independently selected from the group consisting of hydrogen and lower alkyl, provided that when said X is S then said $R_{11}$ is hydrogen;

a 1H-1,2,3,4-tetrazol-1-yl radical of the formula

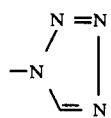  (g); and and
a 4,5-dihydro-5-thioxo-1H-1,2,3,4-tetrazol-1-yl radical of the formula

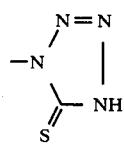  (h).

It is understood that radicals of formula (f) wherein $R_{11}$ stands for hydrogen, as well as the radical of formula (h) may also exist under their tautomeric enol, respectively thienol, forms. Such enol and thienol forms, although not explicitely indicated in the above structures, are naturally intended to be within the scope of formula (I).

As used herein, the term "lower alkyl" denotes straight and branch chained hydrocarbon radicals having from 1 to 6 carbon atoms, such as, for example, methyl, ethyl, 1-methylethyl, 1,1-dimethylethyl, propyl, butyl, pentyl, hexyl and the like; and the term "halo" is generic to halogens of atomic weight less than 127, i.e. fluoro, chloro, bromo and iodo.

Preferred compounds within the scope of formula (I) are those wherein Q is CH and wherein the Y substituent is located at the position of the benzene nucleus which is para to the dioxolanylmethoxy group. Particularly preferred are those compounds wherein Ar represents a halophenyl or di-halophenyl radical, the most preferred being 2,4-dichlorophenyl.

In order to simplify the structural representation of compounds (I) and of certain starting materials and intermediates used in the preparation thereof, the 2-Ar-2-(1H-imidazol-1-ylmethyl or 1H-1,2,4-triazol-1-ylmethyl)-1,3-dioxolan-4-yl group wherein Ar is as previously defined, will hereafter be represented by the symbol D:

The compounds of formula (I) wherein Y is as previously defined but other than a radical of the formula (f) wherein $R_{11}$ is hydrogen and other than a radical of formula (h), said Y being represented by $Y_1$ and said compounds by the formula (I-a), can be prepared by the reaction of an appropriate reactive ester of the formula (II) with an appropriately substituted phenol of formula (III).

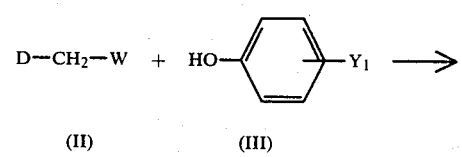

(II)    (III)

D—CH$_2$—O—⟨benzene⟩—Y$_1$ (I-a)

In formula (II), W has the meaning of a reactive ester residue such as, for example, halo, methylsulfonyloxy, 4-methylphenylsulfonyloxy and the like. The reaction of (II) with (III) is carried out under art-known conditions of performing O-alkylations with reactive esters. The reaction is generally carried out in an appropriate reaction-inert organic solvent such as, for example, N,N-dimethylformamide, N,N-dimethylacetamide, hexamethylphosphoric triamide, dimethylsulfoxide, 4-methyl-2-pentanone and the like, optionally in admixture with other reaction inert solvents such as, for example, aromatic hydrocarbons, e.g., benzene, methylbenzene, dimethylbenzene and the like. Further it is advantageous to add to the reaction mixture an appropriate base such as, for example, an alkali metal hydride or carbonate, in order to enhance the rate of the reaction. Otherwise it may be advantageous to first convert the substituted phenol (III) into a metal salt thereof, preferably the sodium salt, in the usual manner, e.g., by the reaction of (III) with metal bases such as sodium hydride, sodium hydroxide and the like, and to use thereafter said metal salt in the reaction with (II). Somewhat elevated temperatures are appropriate to enhance the reaction rate and most preferably the reaction is carried out at from about 80° C. to about 130° C.

Compounds of formula (I) wherein Y has the formula (c) wherein $R_4$ and $R_5$ are as previously defined and $R_3$ is hydrogen, lower alkythio, lower alkylsulfinyl or lower alkylsulfonyl, or, the formula (e), (f), (g) or (h), said Y being represented by $Y_2$ and said compounds by the formula (I-b), can also be prepred by cyclizing an appropriate intermediate (IV) wherein A is an amino group or a derivative thereof, with an appropriate cyclizing agent, and, if desired, introducing suitable substituents into the thus obtained heterocyclic compounds.

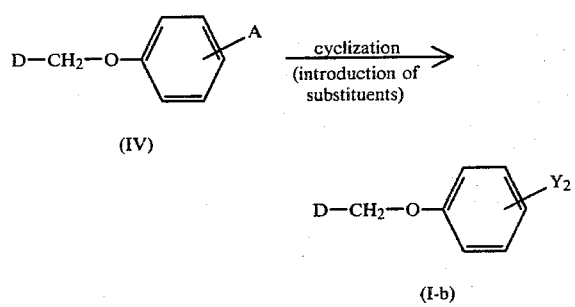

The nature of A in formula (IV), as well as the nature of the cyclizing agent to be used in the cyclization step, depend upon the meaning of $Y_2$ in the desired compounds (I-b) as will be explained hereafter.

Compounds of formula (I-b) wherein $Y_2$ has the formula (c) wherein $R_4$ and $R_5$ have the previously indicated meaning and $R_3$ is hydrogen, lower alkythio, lower alkylsulfinyl or lower alkylsulfonyl, said $R_3$ represented by $R_3'$ and said compounds by (I-b-1), can be derived from an appropriate isothiocyanate of the formula (IV-a) by cyclizing the latter with an appropriate aminoethanone or aminoacetaldehyde of the formula (V) and thereafter introducing appropriate substituents into the thus obtained 1H-imidazole-2-thiol of formula (VI) following art-known procedure

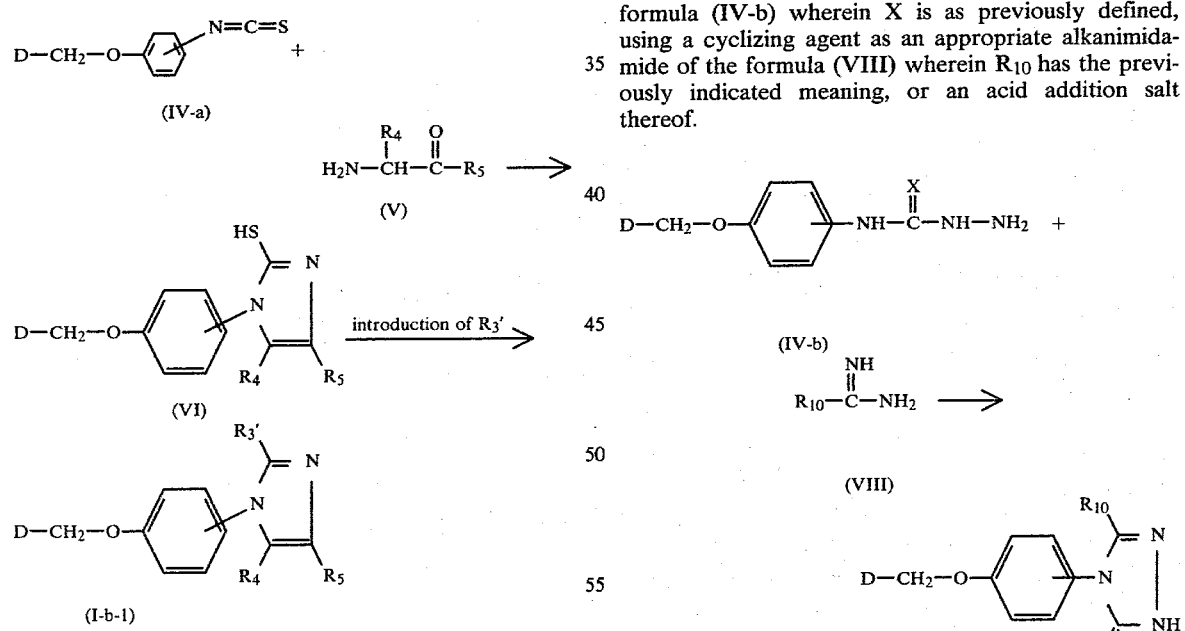

The reaction of (IV-a) with (V) to produce (VI) is conveniently carried out by stirring, preferably under heating, the reactants together in a suitable organic solvent, such as a lower alkanol, e.g. 2-propanol, in the presence of an appropriate base such as, for example, an alkali or earth alkaline metal carbonate or hydrogen carbonate. The introduction of the desired $R_3'$ substituents into (VI) can be accomplished by generally known procedures such as the following.

When $R_3'$ stands for hydrogen the compounds (I-b-1) are easily obtained by desulfurating (VI) in the usual manner, e.g., by treating the latter with Raney-nickel or with diluted nitric acid. When $R_3'$ stands for lower alkythio the compounds (I-b-1) can be obtained by subjecting (IV) to a standard S-alkylation with a suitable reactive ester of the formula (VII).

(lower alkyl)-W    (VII)

wherein W is as previously defined, or, with a di(lower alkyl) sulfate. When $R_3'$ is a lower alkylsulfinyl or lower alkylsulfonyl group the compounds (I-b-1) are obtained by subjecting the corresponding compounds wherein $R_3'$ is lower alkylthio to an oxidation reaction with and appropriate oxidizing agent. Appropriate oxidizing agents to be used therefore include, for example, hydrogen peroxide, optionally substituent benzeneperioxide acids, e.g. 3-chlorobenzeneperoxoic acid, and permananate salts such as potassium permanganate. The degree of oxidation, i.e. repespectively to the sulfoxide or sulfone level, is determined by the ratio of the reagents. When sulfoxides are to be prepared about 2 equivalents of the oxidizing agent are to be used per mole of sulfide while at least 4 equivalents are necessary to produce sulfones. Oxidations with hydrogen peroxide and permanganate salts are preferably carried out in acidic aqueous medium while oxidations with benzeneperoxoic acids are preferably conducted in an appropriate reaction-inert organic solvent, e.g. a halogenated hydrocarbon such as dichloromethane.

Compounds of formula (I-b) wherein $Y_2$ has the formula (f) wherein $R_{11}$ is hydrogen, (I-b-2), are conveniently derived from an appropriate intermediate of the formula (IV-b) wherein X is as previously defined, using a cyclizing agent as an appropriate alkanimidamide of the formula (VIII) wherein $R_{10}$ has the previously indicated meaning, or an acid addition salt thereof.

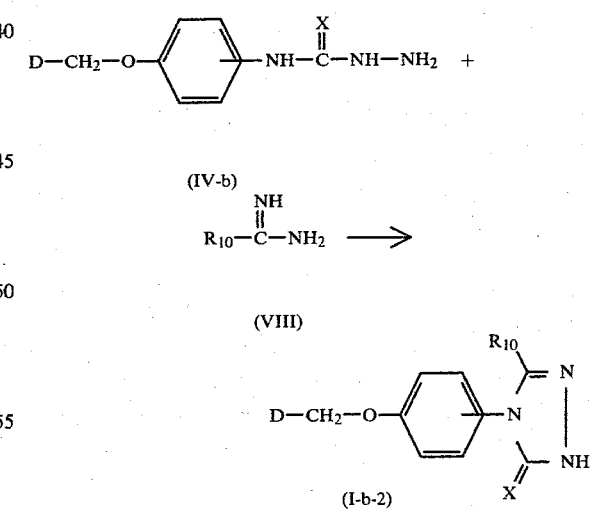

the cyclization reaction may be carried out according to methodologies known in the art, for example, by mixing and melting the reactants together, if desired in the presence of an appropriate reaction-inert organic liquid having a relatively high boiling point such as, for example, 1,1′-oxybis(2-methoxyethane).

Compounds of formula (I-b) wherein $Y_2$ has the formula (f) wherein X is O and $R_{11}$ is lower alkyl (I-b-4), can be prepared by N-alkylating a compound of the formula (I-b-2) wherein X stands for O, (I-b-3), with an appropriate reactive ester of formula (VII).

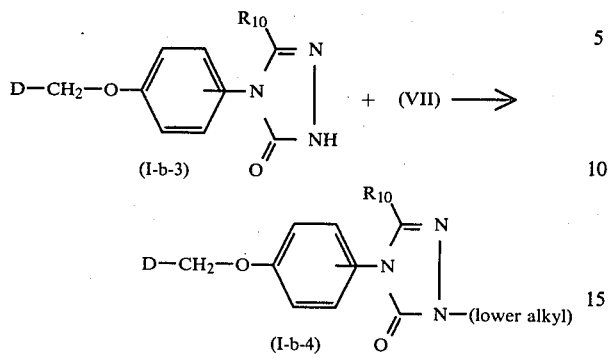

Said N-alkylation may be carried out in the usual manner, e.g. by stirring the reactants together, preferably at somewhat elevated temperatures in an appropriate organic solvent such as, for example, dimethylsulfoxide, in the presence of an appropriate base such as, for example, an alkali metal hydride or carbonate.

The compounds of formula (I-b) wherein $Y_2$ has the formula (e), (I-b-6), can be prepared by introducing $R_8$ into an appropriate compound (I-b-2) wherein X stands for S and $R_{10}$ has the meaning of $R_9$ as previously defined, said starting compounds being represented by the formula (I-b-5).

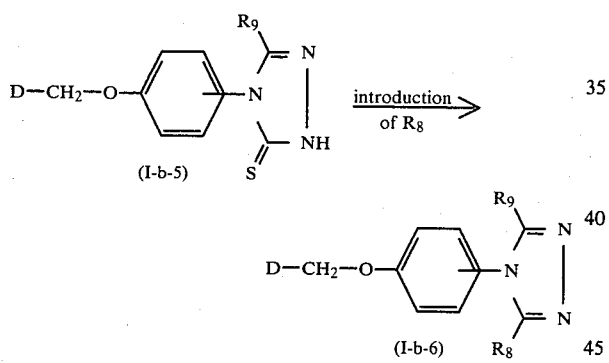

Compounds of the formula (I-b-6) wherein $R_8$ is hydrogen, lower alkylthio, lower alkylsulfinyl or lower alkylsulfonyl are derived from (I-b-5) using similar procedures as described hereinbefore for the preparation of compounds (I-b-1) starting from (VI). Those compounds of formula (I-b-6) wherein $R_8$ is lower alkyloxy can be derived from the corresponding lower alkylsulfonyl substituted compounds by reacting the latter with an appropriate lower alkanol to replace the lower alkylsulfonyl group by a lower alkyloxy group. The reaction is preferably conducted at slightly elevated temperatures in an appropriate relatively polar, organic solvent, such as dimethylsulfoxide, in the presence of strong metal base such as, for example, an alkali or earth alkaline metal hydride.

Compounds of formula (I-B-) wherein $Y_2$ is a radical of formula (g), (I-b-7), can be prepared by the reaction of an intermediate of formula (IV) wherein A stands for an amino group, (IV-c), with an azide, preferably an alkali metal azide, e.g. sodium azide, and an appropriate 1,1′,1″-methylidynetris(oxy)tris(lower alkane) of formula (IX) in an appropriate acidic medium, e.g. acetic acid, preferably under heating.

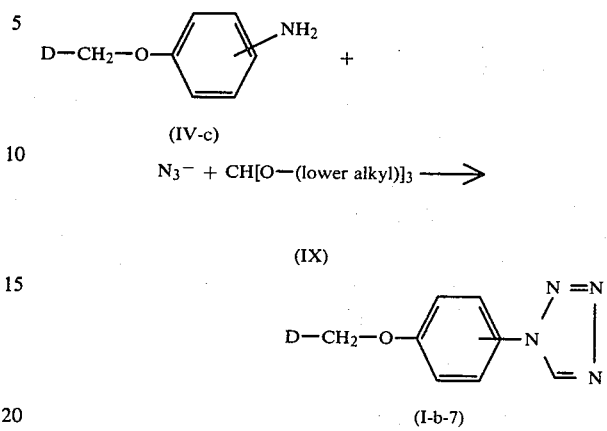

Compounds of formula (I-b) wherein $Y_2$ has the formula (h), (I-b-8), can be obtained by the reaction of an isothiocyanate of formula (IV-a) with an appropriate azide, preferably sodium azide, in a appropriate organic solvent, e.g. a lower alkanol such as methanol, ethanol, 2-propanol and the like in the presence of alkali.

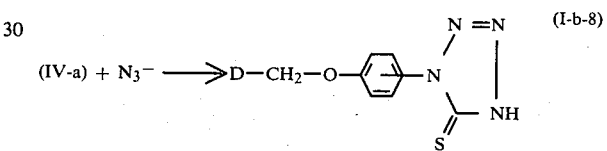

Said cyclization reaction may also be carried out by stirring (IV-a) with the azide in the presence of an appropriate quaternary ammonium salt, preferably N,N,N-triethylbenzenemethanaminium chloride, in a suitable solvent system such as, for example, water, preferably in admixture with an appropriate organic solvent such as, for example, 1,4-dioxane, to better solubilize the reactants.

The imidazole derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, 2-hydroxypropanoic, 2-oxypropanoic, ethanedoic, propanedoic, 1,4-butanedioic, (Z)-2-butenedoic, (E)-2-butenedoic, 2-hydroxy-1,4-butanedoic, 2,3-dihydroxy-1,4-butanedoic, 2-hydroxy-1,2,3-propanedtricarboxylic, benzoic, 3-phenyl-2-propenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

A number of the intermediates and starting materials used in the foregoing preparations are known compounds, others may be prepared according to art-known methodologies of preparing similar compounds and some of them are novel and consequently their preparation will be described hereafter.

Starting materials of formula (III) can in general be derived from the corresponding methoxy-substituted compounds of formula (X) by converting the methoxy group of the latter into a hydroxy group by acid hydrolysis using a strong non-oxidizing mineral acid, such as, for example, hydrobromic acid in acetic acid.

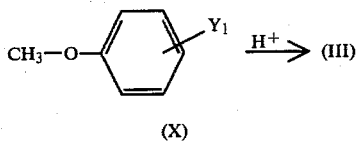

(X)

The intermediates of formula (X), used as starting materials herein can be obtained by a variety of methods, depending on the nature of $Y_1$ in said formation (X).

Intermediates of formula (X) wherein $Y_1$ has the formula (a), (b), (c) or (d), said $Y_1$ being represented by $Y_1'$ and said intermediates by (X-a), can conveniently be prepared by the reaction of an appropriate halo-methoxybenzene of formula (XI) with an appropriate azole of formula (XII).

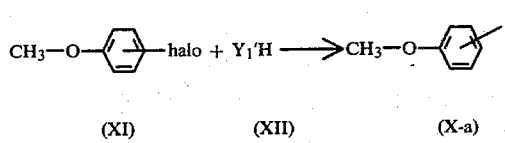

(XI)    (XII)    (X-a)

The reaction of (XI) with (XII) is carried out according to art known procedures, e.g., by stirring the reactants together for from several hours to several days in an appropriate organic solvent such as, for example, N,N-dimethylformamide, N,N-dimethylacetamide, hexamethylphosphoric triamide, dimethylsulfoxide and the like, most preferably in the presence of an appropriate copper(I)salt, e.g. the chloride of the bromide, to enhance the reaction rate.

Those intermediates of formula (X) wherein $Y_1$ has the formula (a) as well as the corresponding phenols of formula (III) can also be prepared according to the method described in Ber. 95, 2270 (1962).

Intermediates of formula (X) wherein $Y_1$ has the formula (b), (X-b), may also be prepared by the reaction of an appropriate (methoxyphenyl)hydrazine of formula (XIII), which is usually employed in the form of an acid addition salt, with an appropriate dione of formula (XIV) wherein $R_1$ and $R_2$ are as previously defined.

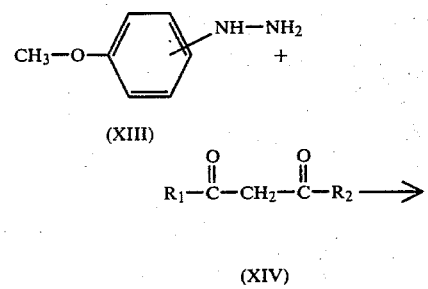

(XIII)

$$R_1-\overset{O}{\underset{\|}{C}}-CH_2-\overset{O}{\underset{\|}{C}}-R_2 \longrightarrow$$

(XIV)

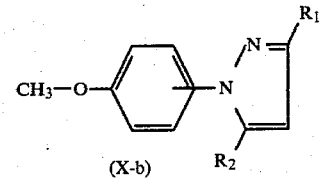

(X-b)

The reaction of (XIII) with (XIV) is conveniently carried out by stirring and refluxing the reactants together in an appropriate organic solvent, e.g. a lower alkanol such as ethanol, preferably but not necessarily in the presence of an appropriate base such as, for example, an alkali metal carbonate, e.g. potassium carbonate. When $R_1$ stands for hydrogen, the adjacent carbonyl group of (XIV) is preferably ketalized prior to reacting said (XIV) with (XIII) in order to obtain a pyrazole derivative wherein $R_2$ is unambigously located at the 5-position. Mixtures of position isomers which can otherwise be obtained when using unketalized aldehydes or ketones of formula (XIV) may be subjected to standard isolation and purification procedures to separate the pure constituents from each other.

Intermediates of formula (X) wherein $Y_1$ stands for a radical of the formula (c) wherein $R_3$ has the meaning of $R_3'$ as previously defined, (X-c), can also be derived from an appropriate isothiocyanate of the formula (XV) by cyclizing the latter with an appropriate aminoethanone of the formula (V) and thereafter introducing the desired $R_3'$-substituents into the thus obtained (XVI) following similar procedures as previously described herein for the preparation of compounds (I-b-1) starting from (IV-a)

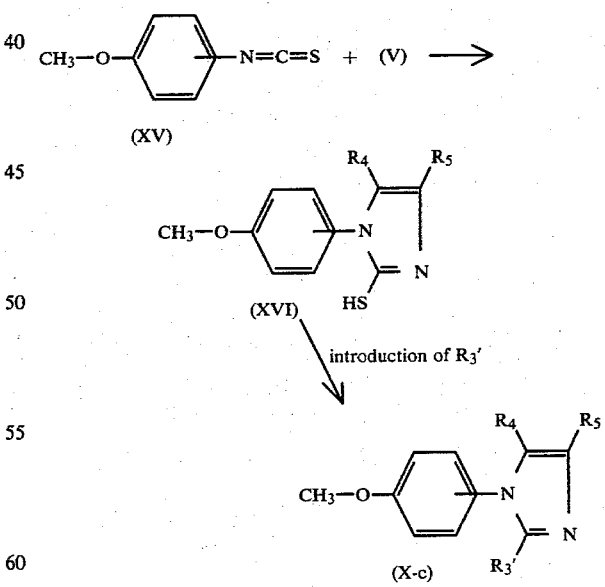

Intermediates of formula (X) wherein $Y_1$ stands for a radical of formula (d), (X-d), can also be prepared starting from an appropriate 1-(methoxyphenyl)-1H-1,2,4-triazole-3-thiol of formula (XVII) by desulfurating or S-alkylating the latter in the usual manner to obtain (X-d) wherein $R_6$ is hydrogen or lower alkylthio.

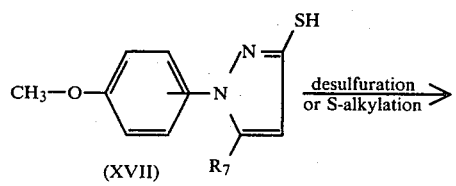

The 1H-1,2,4-triazole-3-thiols of formula (XVII) used as starting materials herein can be derived from an appropriate 2-(methoxyphenyl)hydrazinecarbothioamide of formula (XVIII) by cyclizing the latter with an appropriate carboxylic acid of the formula $$R_7-\overset{O}{\underset{\|}{C}}-OH \qquad (XIX)$$

or a functional derivative thereof, such as, for example, an acyl halide, an ester, or preferably an imidamide of the formula $$R_7-\overset{NH}{\underset{\|}{C}}-NH_2 \qquad (XIX\text{-}a)$$

The reaction is conveniently carried out by stirring and heating the reactants together in an appropriate organic solvent, e.g. a lower alkanol such as, for example, 2-propanol, butanol and the like.

Alternatively the same compounds (XVII) can be obtained by first acylating (XVIII) with an appropriate anhydride (XX) or acyl halide (XIX-b) derived from an acid of formula (XIX), to obtain an intermediate of formula (XXI), and, thereafter cyclizing the latter by stirring and heating (XXI) in alcoholic alkali. The foregoing reaction are schematically represented as follows:

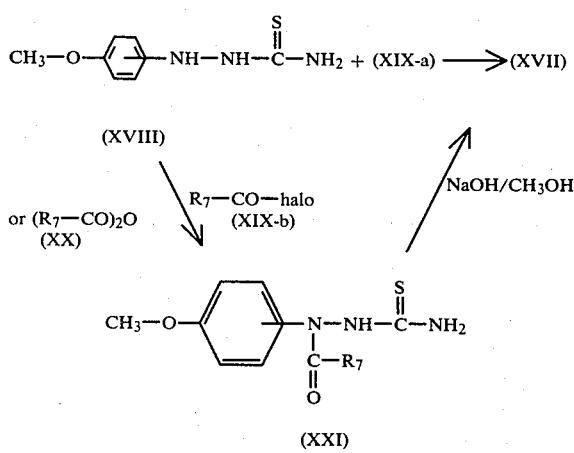

Still another method of preparing the compounds of formula (XVII) is by reacting a hydrazine hydrochloride of formula (XIII-a) with an acyl isothiocyanate of formula (XXII) in N,N-diethylethanamine, washing the reaction mixture with water, evaporating off the solvent and thereafter stirring and heating the residue in a mixture of dichloromethane and ethanol in the presence of alkali.

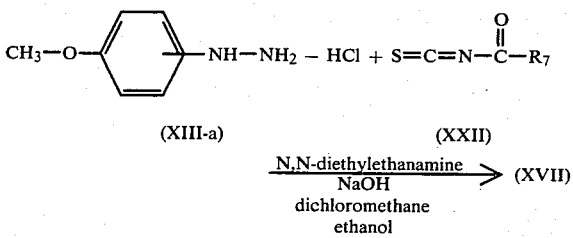

Intermediates of formula (X) wherein $Y_1$ is a radical of the formula (e) or (f) can easily be derived from a N-(methoxyphenyl)hydrazinecarboxamide or carbothioamide of the formula

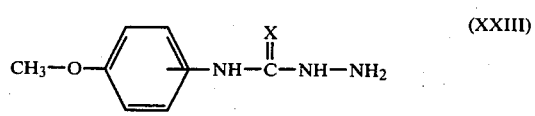

by the application of similar procedures as previously described herein for the preparation of compounds (I-b-2), (I-b-4) and (I-b-6) starting from (IV-b).

Intermediates of formula (X) wherein $Y_1$ is a radical of formula (g) can be derived from a methoxybenzenamine of the formula

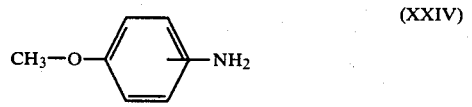

following the procedures described herein for the preparation of compounds (I-b-7) starting from (IV-c).

The precursor materials of the formulae (XIII), (XV) and (XXIV) herein are generally known and may be prepared following methods described in the literature.

The precursor materials of formula (XVIII) are easily prepared by the reaction of the corresponding hydrazine hydrochloride with potassium isothiocyanate, according to the procedure described in C.A., 59, 8651 b (1963) wherein the 4-substituted analog is specifically described.

The precursor materials of formula (XXIII) wherein X stands for S, (XXIII-a), are described in C.A., 18, 3788 (1924); C.A., 47, 3342i (1953); C.A. 56, P 3681a (1962); C. A., 51, 12016h (1957) and J. Am. Chem. Soc. 70, 3439 (1948).

The precursor materials of formula (XXIII) wherein X stands for O, (XXIII-b), are easily obtained by the reaction of a phenyl (methoxyphenyl)carbamate (XXV) with hydrazine hydrate

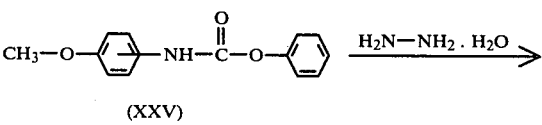

-continued

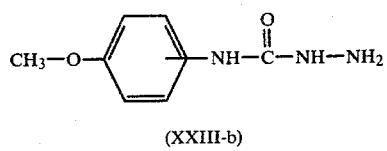

(XXIII-b)

The carbamates of formula (XXV) are conveniently prepared by the reaction of a benzenamine of formula (XXIV) with phenyl carbonochloridate. The compound of formula (XXIII-b) wherein the methoxy group is located at the para-position is described in C. A., 31, 3891[8] (1937).

Starting materials of formula (II) wherein Q stands for CH and methods of preparing the same are described in Belg. Pat. No. 837,831. In general the reactive esters of formula (II) can be prepared along the following sequence of reactions.

An appropriate 1-Ar-2-bromoethanone of formula (XXVI) is subjected to a ketalization reaction with 1,2,3-propanetriol following methodologies analogous to those described in Synthesis, 1974 (I), 23.

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as cyclohexane.

The thus obtained dioxolane (XXVII) is then reacted with benzoyl chloride to obtain a benzoate of the formula (XXVIII) and the latter is subsequently reacted with 1H-imidazole or 1H-1,2,4-triazole. Said reaction is preferably carried out by stirring and heating the reactants together in a suitable organic solvent, e.g N,N-dimethylformamide, in the presence of an appropriate strong metal base, e.g. sodium methanolate to obtain an intermediate of the formula (XXIX). The desired reactive esters of formula (II) are then conveniently prepared by first hydrolyzing (XXIX) in alkaline medium and thereafter converting the hydroxy group of the thus obtained (XXX) into a reactive ester thereof according to methodologies generally known in the art. For example, methanesulfonates and 4-methylbenzenesulfonates are conveniently prepared by the reaction of the alcohol with methanesulfonyl chloride or 4-methylbenzenesulfonyl chloride and halides may be prepared by the reaction of the alcohol with an appropriate halogenating agent such as, for example, sulfuryl chloride, phosphor pentachloride, phosphor pentabromide, phosphoryl chloride and the like. When the reactive ester is an iodide, it is preferably prepared from the corresponding chloride or bromide by the replacement of that halogen with iodine.

The foregoing reactions may be illustrated as follows:

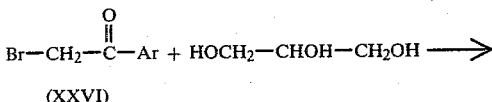

(XXVI)

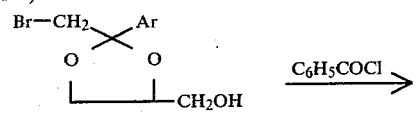

(XXVII)

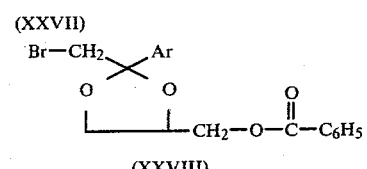

(XXVIII)

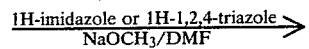

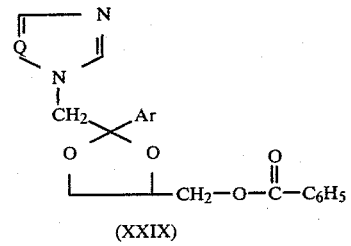

(XXIX)

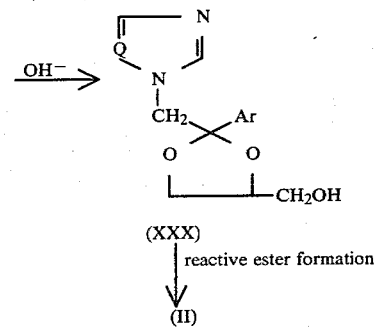

(XXX)

| reactive ester formation
↓
(II)

Intermediates of formula (IV) may be obtained along the following reaction sequence.

An appropriate reactive ester of the formula (II) is reacted in the usual manner with a N-(hydroxyphenyl-)acetamide, (XXXI), to obtain an intermediate of formula (XXXII); the amide group of which is subjected to alkaline hydrolysis, e.g., with alkanolic alkali, to obtain the corresponding amine, (IV-c).

Intermediates of formula (IV) wherein A stands for isothiocyanato, (IV-a), are easily derived therefrom by the application of art-known methods of preparing isothiocyanates from amines, e.g., by the reaction of (IV-c) with carbon disulfide and N,N'-methanetetraylbis(cyclohexanamine) in pyridine.

Intermediates (IV) wherein A stands for a hydrazinecarbothioamide group, (IV-b-1), can be derived from (IV-a) by the reaction thereof with hydrazine hydrate.

Intermediates (IV) wherein A stands for a hydrazinecarboxamide group, (IV-b-2), can be prepared by first converting (IV-c) into a phenyl carbamate (XXXIII) by the reaction of the former with phenyl carbonochloridate and subsequent reaction of said (XXXIII) with hydrazine hydrate.

The foregoing reactions are schematically illustrated hereafter.

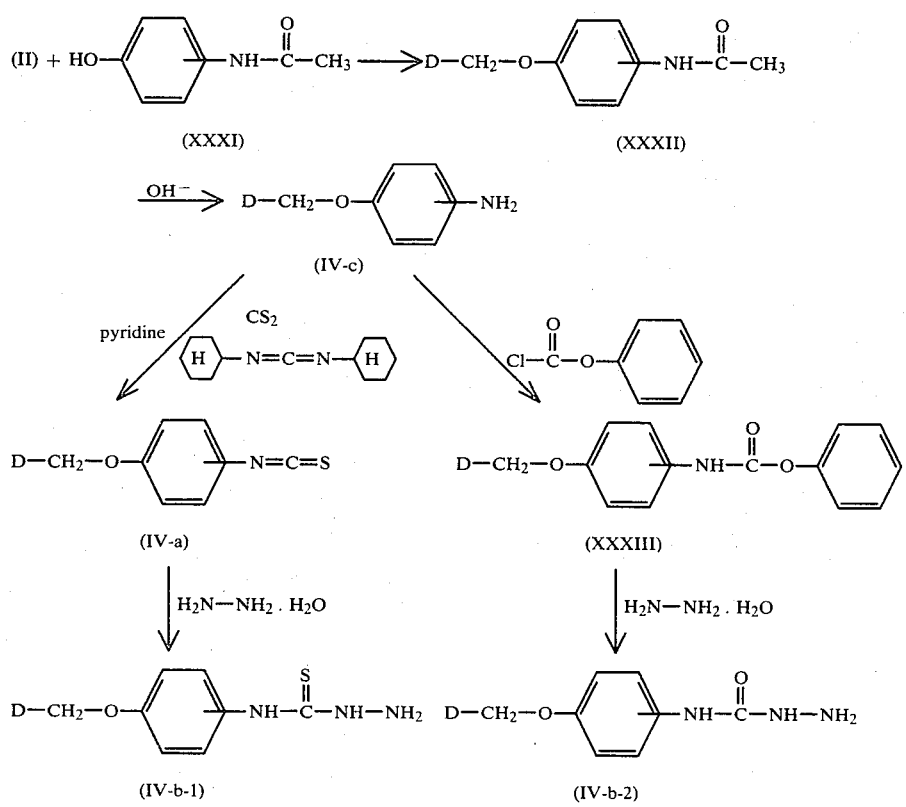

The intermediates of formulae (IV-b-1) and (IV-b-2) and the stereochemically isomeric forms thereof are deemed to be novel, and, as useful intermediates herein they constitute an additional feature of this invention. The intermediates of formulae (IV-a), (XXXII), (IV-c) and (XXXIII) are also deemed to be novel and, apart from their utility as intermediates herein, they possess themselves antifugal and antibacterial properties, and, as such they are described and claimed in our U.S. Pat. Application Ser. No. 764,263 filed Jan. 31, 1977 now abandoned and subsequently filed as a continuation-in-part application Ser. No. 853,728, filed Nov. 21, 1977, now U.S. Pat. No. 4,144,346, granted Mar. 13, 1979.

From formula (I) it is evident that the compounds of this invention have at least two asymmetric carbon atoms in their structures, namely those located in the 2- and 4-position of the dioxolane nucleus, and consequently they can exist under different stereochemically isomeric forms. The stereochemically isomeric forms of (I) and the pharmaceutically acceptable acid addition salts thereof are intended to be within the scope of this invention.

The diastereomeric racemates of (I), denoted as cis and trans forms respectively, according to the rules described in C.A., 76, Index Guide, Section IV, p. 85 (1972), may be obtained separately by conventional methods. Appropriate methods which may advantageously be employed therefore include, for example, selective crystallization and chromatographic separation, e.g. column-chromatography.

Since the stereochemical configuration is already fixed in the intermediates (II) and (IV) it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereabove for the separation of cis and trans forms of the compounds (I).

It is evident that the cis and trans diastereomeric racemates may be further resolved into their optical isomers, cis(+), cis(−), trans(+) and trans(−) by the application of methodologies known to those skilled in the art.

The compounds of formula (I) and the pharmaceutically acceptable acid addition salts thereof are useful agents in combatting fungi and bacteria. For example, said compounds and acid addition salts thereof were found to be highly active against a wide variety of fungi such as, for example, *Microsporum canis, Ctenomyces mentagrophytes, Trichophyton rubrum, Phialophora verrucosa, Cryptococcus neoformans, Candida tropicalis, Candida albicans,* Mucor species, *Aspergillus fumigatus, Sporotrichum schenckii* and Saprolegnia species, and against bacteria such as, for example, *Erysipelotrix insidiosa,* Staphylococci such as *Staphylococcus hemolyticus* and Streptococci such as *Streptococcus pyogenes.* In view of their potent, local as well as systemic, antimicrobial activity for the compounds of this invention constitute useful tools for the destruction or prevention of the growth of fungi and bacteria and more particularly they can effectively be used in the treatment of subjects suffering from such microorganism.

The strong antimicrobial activity of the compounds (I) is clearly evidenced by the data obtained in the following experiments, which data is only given to illustrate the useful antimicrobial properties of all the compounds (I) and not to limit the invention either with respect to the scope of susceptible microorganisms nor with respect to the scope of formula (I).

Experiment A: Activity of compounds (I) against vaginal candidosis in rats.

Female Wistar rats of ±100 g body weight were used. They were ovariectomized and hysterectomized and after three weeks of recovery, 100 μg of oestradiol undecylate in sesame oil was given subcutaneously once a week for 3 consecutive weeks. The thus induced pseudooestrus was controlled by microscopic examination of vaginal smears. Food and water were left available ad libitum.

The rats were infected intravaginally with $8.10^5$ cells of *Candida albicans*, grown on Sabouraud broth for 48 hours at 37° C. and diluted with saline. The date of infection varied from day +25 to day +32 after surgical intervention, depending on the appearance of signs of induced pseudo-oestrus.

The drugs under investigation were administered orally once a day for two days starting from the day of infection. For each experiment there were placebo treated controls. The results were assessed by taking vaginal smears with sterile swabs on several days after the infection. The swabs were put into Sabouraud broth in petri-dishes and incubated for 48 hours at 37° C. If no growth of *Candida albicans* occured, i.e., when the animals were negative at the end of the experiment, this was due to drug administration because it never happened in placebo treated controls.

The tables I and II below give the lowest oral dose of the drug under investigation which was found active at the 14th day after infection.

Experiment B: Activity of compounds (I) against crop candidosis in turkeys.

Turkeys of 14 days old were infected in the crop with $4.10^6$ *Candida albicans* cells, grown on Sabouraud broth for 48 hours at 37° C. and diluted with saline. The volume of the inoculum was 1 ml. The drug under investigation were premixed in 500 mg of lacton and thereafter admixed in 1000 g of meal without any additives. The concentration of the drug under investigation in the meal was expressed in mg/kg.

The animals were given the medicated feed for 13 consecutive days starting on the day of infection. At the end of the experiment all animals were sacrificed. At autopsy the crops were removed, emptied and grinded in an ultra-turrax mixer of 15 ml of sterile saline. Colony counting was done on Sabouraud agar and the results given in Tables I and II represent the $ED_{50}$, i.e., the dose of the drug whereby the crops of 50% of the animals were completely negative for *Candida albicans*.

TABLE I

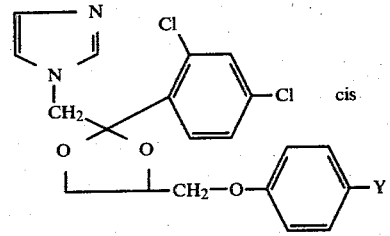

| Y | Base or Salt | Vaginal candidosis in rats: lowest effective dose in mg/kg. | Crop candidosis in Turkeys: $ED_{50}$ in mg/kg of feed. |
|---|---|---|---|
| −N⟨N⟩ (triazole) | base | 1.25 | 8 |
| −N⟨N-N⟩ (tetrazole) | base | 1.25 | 16 |
| −N⟨ ⟩ (pyrrolidine/pyrrole) | base | 2.50 | 125 |
| −N⟨N⟩ | base | 2.50 | 16 |
| −N⟨=N⟩ CH₃ | base | 10 | 125 |

TABLE I-continued

[Structure: cis-configured compound with imidazole, 2,4-dichlorophenyl, dioxolane, and CH₂-O-phenyl-Y groups]

| Y | Base or Salt | Vaginal candidosis in rats: lowest effective dose in mg/kg. | Crop candidosis in Turkeys: ED₅₀ in mg/kg of feed. |
| --- | --- | --- | --- |
| −N−(CH=N)−phenyl group | 2 . HNO₃ | 5 | 125 |
| −N−C(CH₃)=N−NH−C(=O)− (cyclic) | base | <10 | — |
| −N−CH=N−N(−(CH₂)₂−CH₃)−C(=O)− (cyclic) | base | <10 | — |
| −N−CH=N−N(−CH(CH₃)₂)−C(=O)− (cyclic) | base | <10 | — |
| −N−C(CH₃)=N−N(−CH₃)−C(=O)− (cyclic) | HNO₃ | 1.25 | — |
| −N−C(CH₃)=N−N(−CH(CH₃)₂)−C(=O)− (cyclic) | base | 5 | — |
| −N−CH=N−N(−CH₂−CH₃)−C(=O)− (cyclic) | base | 5 | 31 |
| −N−C(CH₃)=N−N(−CH₂−CH₃)−C(=O)− (cyclic) | base | 2.5 | — |

TABLE I-continued
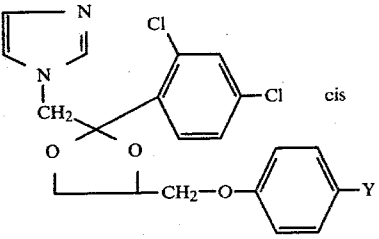
| Y | Base or Salt | Vaginal candidosis in rats: lowest effective dose in mg/kg. | Crop candidosis in Turkeys: ED$_{50}$ in mg/kg of feed. |
|---|---|---|---|
|  | base | 2.5 | — |
|  | base | 10 | 8 |
|  | 2HNO$_3$ | 5 | — |
|  | 2HNO$_3$ | 5 | 31 |
|  | 2HNO$_3$ | 5 | 31 |
|  | 2HNO$_3$ | — | 31 |
|  | 2HNO$_3$ | — | 31 |
|  | 2HNO$_3$ | 1.25 | 16 |
|  | HNO$_3$ . H$_2$O | 10 | — |

TABLE I-continued
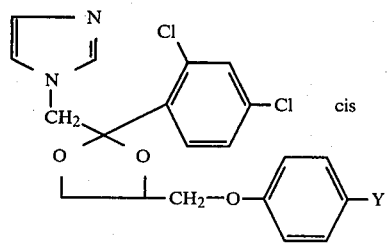
| Y | Base or Salt | Vaginal candidosis in rats: lowest effective dose in mg/kg. | Crop candidosis in Turkeys: ED$_{50}$ in mg/kg of feed. |
|---|---|---|---|
| ![S—CH₃, N—N, CH₃, N] | HNO$_3$ | 2.5 | — |
| ![CH₃, N—N] | HNO$_3$ | 2.5 | — |
| ![S—CH₃, N—N, CH₃, N] | 2HNO$_3$ | 2.5 | — |
| ![N—N, CH₃, N] | 2HNO$_3$ | 1.25 | 8 |
| ![CH₃, O=S=O, N—N] | base H$_2$O | 5 | — |
| ![O—CH₂—CH₃, N—N, N] | 2(COOH)$_2$ | 2.5 | 31 |
| ![N—N, CH₂—CH₃, N] | 2HNO$_3$ | 5 | 8 |
| ![CH₃, S=O, N—N, N] | 1½ (COOH)$_2$ | 2.5 | — |

TABLE I-continued

[Structure: imidazole-N-CH2-C(cis)(2,4-dichlorophenyl) with dioxolane ring CH2-O-C6H4-Y]

| Y | Base or Salt | Vaginal candidosis in rats: lowest effective dose in mg/kg. | Crop candidosis in Turkeys: ED$_{50}$ in mg/kg of feed. |
|---|---|---|---|
| -S(=O)-C(CH3)=N-N=C(CH3)- (4-substituted 3-methyl-4H-1,2,4-triazol-... with S=O, CH3) | (COOH)$_2$ · ½ CH$_3$-CH(OH)-CH$_3$ | 10 | 16 |
| -N(–N=N–N=)— (tetrazolyl) | base | — | 31 |

TABLE II

| | | | Compounds of formula I | | |
|---|---|---|---|---|---|
| Q | Ar | Y | Base or Salt | Vaginal candidosis in rats: lowest effective dose in mg/kg | Crop candidosis in Turkeys: ED$_{50}$ in mg/kg in feed |
| CH | 4-OCH$_3$—C$_6$H$_4$ | 4-(—N⟨=N⟩) | base | 5 | — |
| CH | 2,4-Cl$_2$—C$_6$H$_3$ | 3-(—N⟨=N⟩) | 2(COOH)$_2$ | 2.5 | — |
| N | 2,4-Cl$_2$—C$_6$H$_3$ | 4-(—N⟨=N⟩) | base | 1.25 | 8 |

In view of their antifungal and antibacterial properties this invention provides valuable compositions comprising the subject compounds of formula (I) or acid addition salts thereof as the active ingredient in a solvent or a solid, semi-solid or liquid diluent or carrier, and, in addition, it provides an effective method of combatting fungal or bacterial growth by use of an effective antifungal or antibacterial amount of such compounds (I) or salts thereof. Antifungal and antibacterial compositions comprising an effective amount of an active compound (I), either alone or in combination with other active therapeutic ingredients, in admixture with suitable carriers may be readily prepared according to conventional pharmacuetical techniques for the usual routes of administration.

Preferred compositions are in dosage unit form, comprising per dosage unit an effective quantity of the active ingredient in admixture with suitable carriers. Although the amount of the active ingredient per unit dosage may vary within rather wide limits, dosage units comprising from about 50 to about 500 mg and more particularly from about 100 to about 250 mg of the active ingredient are preferred.

The following examples are intended to illustrate and not to limit the scope of the present invention.

Unless otherwise stated all parts therein are by weight.

EXAMPLE I

A mixture of 16.4 parts of 2-methyl-1H-imidazole, 37.4 parts of 1-bromo-4-methoxybenzene, 1 part of copper (I) bromide, 20 parts of potassium carbonated and 270 parts of N,N-dimethylformamide is stirred and refluxed for one week. The reaction mixture is cooled, poured onto water and the whole is extracted with 2,2'-oxybispropane. The extract is washed twice with a diluted hydrochloric acid solution. The acid aqueous phase is separated and alkalized with sodium hydroxide. The product is extracted twice with 2,2'-oxybispropane. The combined extracts are dried, filtered and evaporated, yielding 4 parts (41%) of 1-(4-methoxyphenyl)-2-methyl-1H-imidazole as a residue.

A mixture of 4 parts of 1-(4-methoxyphenyl)-2-methyl-1H-imidazole and 37.5 parts of hydrobromic acid solution 48% is stirred and refluxed overnight. After cooling, the reaction mixture is evaporated. The residue is triturated in a mixture of 2-propanone and 2,2'-oxybispropane. The product is filtered off and crystallized from a mixture of ethanol and 2,2'-oxybispropane, yielding 3.8 parts (69%) of 4-(2-methyl-1H-imidazol-1-yl)phenol monohydrobromide; mp. 181–205° C.

EXAMPLE II

A mixture of 19.2 parts of 2-ethyl-1H-imidazole, 37.4 parts of 1-bromo-4-methoxybenzene, 1 part of copper-(I)iodide, 20 parts of potassium iodide and 180 parts of N,N-dimethylacetamide is stirred and refluxed for one week. The reaction mixture is cooled, diluted with water and the product is extracted with 2,2'-oxybispropane. After filtration over hyflo, the extract is separated from the aqueous phase and acidified with a concentrated nitric acid solution. The formed nitrate salt is filtered off and crystallized from a mixture of ethanol and 2,2'-oxybispropane, yielding 6.2 parts (12%) of 2-ethyl-1-(4-methoxyphenyl)-1H-imidazole mononitrate; mp. 132.6° C.

A mixture of 5.2 parts of 2-ethyl-1-(4-methoxyphenyl)-1H-imidazole and 75 parts of hydrobromic acid solution 48% in glacial acetic acid is stirred and refluxed overnight. The solvent is evaporated and the residue is triturated in 2-propanone. The product is filtered off and dried, yielding 6.1 parts (100%) of 4-(2-ethyl-1H-imidazol-1-yl)phenol monohydrobromide.

EXAMPLE III

A mixture of 28.8 parts of 2-phenyl-1H-imidazole, 37.4 parts of 1-bromo-4-methoxybenzene, 20 parts of potassium carbonate and 180 parts of N,N-dimethylacetamide is stirred for one week at reflux temperature. The reaction mixture is cooled, poured onto water and the product is extracted twice with 2,2'-oxybispropane. The combined extracts are dried, filtered and evaporated, yielding 10 parts (25%) of 1-(4-methoxyphenyl)-2-phenyl-1H-imidazole as a residue.

A mixture of 10 parts of 1-(4-methoxyphenyl)-2-phenyl-1H-imidazole and 150 parts of a hydrobromic acid solution 48% is stirred and refluxed overnight. The solvent is removed in vacuo and the residue is dissolved in methanol. The solution is saturated with a small excess of sodium hydroxide. After the addition of 2,2'-oxybispropane, the product is precipitated. It is filtered off and dried, yielding 7.9 parts (76%) of sodium 4-(2-phenyl-1H-imidazol-1-yl)phenolate.

EXAMPLE IV

A mixture of 13.8 parts of 1H-1,2,4-triazole, 18.7 parts of 1-bromo-4-methoxybenzene, 5 parts of potassium carbonate, 0.5 parts of copper (I) chloride and 90 parts of N,N-dimethylformamide is stirred and refluxed for 2 days. The reaction mixture is cooled and poured onto water. The product is extracted twice with benzene. The combined extracts are washed with water dried, filtered and evaporated. The residue is purified by column-chromatography over silica gel using trichloromethane as eluent. The pure fractions are collected and the eluent is evaporated. The residue is triturated in 2,2'-oxybispropane. The product is filtered off and dried, yielding 7.8 parts (44.5%) of 1-(4-methoxyphenyl)-1H-1,2,4-triazole; mp. 99.4° C.

A mixture of 8 parts of 1-(4-methoxyphenyl)-1H-1,2,4-triazole and 150 parts of a hydrobromic acid solution 48% is stirred and refluxed overnight. The reaction mixture is evaporated and the residue is triturated in 2-propanone. The product is filtered off and crystallized from ethanol, yielding 5.5 parts (74%) of 4-(1H-1,2,4-triazol-1-yl)phenol; mp. 255.4° C. EXAMPLE V A mixture of 1.7 parts of N-(4-hydroxyphenyl)-acetamide, 4.2 parts of cis-2-(2,4-dichlorophenyl)-2- (1H-imidazol-1-ylmethyl)-1,3-dioxolan-4-ylmethyl methanesulfonate, 2 parts of potassium carbonate and 68 parts of N,N-dimethylformamide is stirred overnight at 100° C. The reaction mixture is cooled and poured onto water. The product is extracted twice with trichloromethane. The combined extracts are washed twice with water, dried, filtered and evaporated. The residue is triturated in a mixture of 4-methyl-2-pentanone and 2,2'-oxybispropane. The product is filtered off and crystallized from 4-methyl-2-pentanone, yielding 2.8 parts (61%) of cis-N-{4-[2-(2,4-dichlorophenyl)-2-(1H-imidazol-1-ylmethyl)-1,3-dioxolan-4-ylmethoxy]phenyl}acetamide; mp. 180.5° C.

A mixture of 8.9 parts of cis-N-{4-[2-(2,4-dichlorophenyl)-2-(1H-imidazol-1-ylmethyl)-1,3-dioxolan-4-ylmethoxy]phenyl}acetamide, 1.5 parts of potassium hydroxide and 80 parts of 1-butanol is stirred and refluxed overnight. The reaction mixture is evaporated and water is added to the residue. The precipitated product is filtered off and crystallized from methylbenzene, yielding 6.6 parts (82%) of cis-4-[2-(2,4-dichlorophenyl)-2-(1H-imidazol-1-ylmethyl)-1,3-dioxolan-4-ylmethyl]benzenamine; mp. 164.4° C.

EXAMPLE VI

To a stirred and cooled (ice-bath) solution of 8.4 parts of cis-4-[2-(2,4-dichlorophenyl)-2-(1H-imidazol-1-ylmethyl)-1,3-dioxolan-4-ylmethoxy]benzenamine in 75 parts of pyridine and 112 parts of trichloromethane are added dropwise 3.5 parts of phenyl carbonochloridate. Upon completion, stirring is continued for 3 hours at room temperature. The reaction mixture is poured onto water and the product is extracted twice with trichloromethane. The combined extracts are dried, filtered and evaporated. The residue is triturated in a mixture of 1,1'-oxybisethane and 2,2'-oxybispropane. The product is filtered off and crystallized from 4-methyl-2-pentanone, yielding 8.6 parts of cis-phenyl }4-[2-(2,4-dichlorophenyl)-2-(1H-imidazol-1-ylmethyl)-1,3-dioxolan-4-ylmethoxy]phenyl}carbamate; mp. 170.6° C.

A mixture of 50 parts of hydrazine hydrate, 6 parts of cis-phenyl {4-[2-(2,4-dichlorophenyl)-2-(1H-imidazol-1-ylmethyl)-1,3-dioxolan-4-ylmethoxy]penyl}carbamate and 100 parts of 1,4-dioxane is stirred and refluxed for 2 hours. The reaction mixture is cooled, poured onto water and stirred till the product is precipitated. It is filtered off and crystallized from ethanol, yielding 4.8 parts (91%) of cis N-{4-[2-(2,4-dichlorophenyl)-2-(1H-imidazol-1-ylmethyl)-1,3-dioxolan-4-ylmethoxy]-phenyl}hydrazinecarboxamide hemihydrate; mp. 187.5° C.

EXAMPLE VII

To a stirred and cooled (ice-salt bath) solution of 13 parts of carbon disulfide and 2.1 parts of N,N'-methanetetraylbis[cyclohexanamine] in 15 parts of pyridine is added dropwise a solution of 4.2 parts of cis-4-[2-

(2,4-dichlorophenyl)-2-(1H-imidazol-1-ylmethyl)-1,3-dioxolan-4-ylmethoxy]benzenamine in 25 parts of pyridine at a temperature between −10° C. and −5° C. Upon completion, stirring is continued first at −10°−−5° C. for 3 hours and further at room temperature for one hour. The reaction mixture is evaporated. The residue is dissolved in 20 parts of acetic acid. The solution is stirred and 50 parts of water are added. The formed precipitate is filtered off and the filtrate is neutralized with potassium carbonate. The product is extracted with 1,1′-oxybisethane. The extract is dried, filtered and evaporated. The residue is purified by column-chromatography over silica gel using trichloromethane as eluent. The pure fractions are collected and the eluent is evaporated. The residue is crystallized from a mixture of 4-methyl-2-pentanone and 2,2′-oxybisporpane. The product is filtered off and dried, yielding 3.2 parts (69%) of cis-1-[2-(2,4-dichlorophenyl)-4-(4-isothiocyanatophenoxymethyl)-1,3-dioxolan-2-ylmethyl]-1H-imidazole; mp. 136° C.

To a stirred solution of 14 parts of cis-1-[2-(2,4-dichlorophenyl)-4-(4-isothiocyanatophenoxymethyl)-1,3-dioxolan-2-ylmethyl]-1H-imidazole in 160 parts of methanol are added 7.5 parts of hydrazine hydrate. Stirring is continued for two hours at room temperature. The precipitated product is filtered off, washed with methanol, dried and crystallized from ethanol, yielding 10.7 parts of cis-N- {4-[2-(2,4-dichlorophenyl)-2-(1H-imidazol-1-ylmethyl)-1,3-dioxolan-4-ylmethoxy]-phenyl }hydrazinecarbothioamide; mp. 167.3° C.

EXAMPLE VIII

A mixture of 1.8 parts of 4-(1H-imidazol-1-yl)phenol, 4.2 parts of cis-2-(2,4-dichlorophenyl)-2-(1H-imidazol-1-ylmethyl)-1,3-dioxolan-4-ylmethyl methanesulfonate, 2 parts of potassium carbonate and 68 parts of N,N-dimethylformamide is stirred overnight at 100° C. The reaction mixture is cooled and poured onto water. The product is extracted twice with benezene. The combined extracts are washed with water, dried, filtered and evaporated. The residue is converted into the nitrate salt in 2-propanone. The salt is filtered off and crystallized from ethanol, yielding 3.5 parts (59%) of cis-1-{4-[2-(2,4-dichlorophenyl)-2-(1H-imidazol-1-ylmethyl)-1,3-dioxolan-4-ylmethoxy]phenyl }-1H-imidazole nitrate; mp. 191.1° C.

EXAMPLE IX

Following the procedure of Example VIII and using equivalent amounts of the appropriate starting materials, the following compounds are obtained in free base form or in the form of an acid addition salt after reaction of the free base with an appropriate acid:
cis-1-{2-(2,4-dichlorophenyl)-4-[4-(1H-pyrrol-1-yl)-phenoxymethyl]-1,3-dioxolan-2-ylmethyl}-1H-imidazole; mp. 149.8° C;
cis-1-{4-[2-(2,4-dichlorophenyl)-2-(1H-imidazol-1-yl-methyl)-1,3-dioxolan-4-ylmethoxy]phenyl}-1H-pyrazole; mp. 135.6° C.; and
cis-1-{4-[2-(2,4-dichlorophenyl)-2-(1H-imidazol-1-yl-methyl)-1,3-dioxolan-4-ylmethoxy]phenyl}-1H-1,2,4-triazole; mp. 140.1° C.

EXAMPLE X

A mixture of 2.8 parts of sodium 4-(2-phenyl-1H-imidazol-1yl)phenolate, 4.2 parts of cis-2-(2,4-dichlorophenyl)-2-(1H-imidazol-1-ylmethyl)-1,3-dioxolan-4-ylmethyl methanesulfonate and 100 parts of dimethylsulfoxide is stirred overnight at 100° C. The reaction mixture is cooled and poured onto water. The product is extracted twice with benzene. The combined extracts are dried, filtered and evaporated. The residue is converted into the nitrate in 4-methyl-2-pentanone and 2,2′-oxybispropane. The salt is filtered off and crystallized from a mixture of ethanol and 2,2′-oxybispropane. The salt is filtered off and crystallized from a mixture of ethanol and 2,2′-oxybispropane, yielding 3.7 parts (55%) of cis 1-{4-[2-(2,4-dichlorophenyl)-2-(1H-imidazol-1-ylmethyl)-1,3-dioxolan-4-ylmethoxy]phenyl}-2-phenyl-1H-imidazole dinitrate; mp. 191.8° C.

EXAMPLE XI

To a stirred suspension of 1.6 parts of sodium hydride dispersion 78% in 200 parts of dimethylsulfoxide and 45 parts of benzene are added 7.6 parts of 4-(1H-imidazol-1-yl)phenol and stirring is continued for one hour at 50° C. Then there are added 16.8 parts of cis-2-(2,4-dichlorophenyl)-2-(1H-imidazol-1-ylmethyl)-1,3-dioxolan-4-ylmethyl methanesulfonate. After stirring for 6 hours at 100° C., the reaction mixture is cooled, poured onto water and the product is extracted with benzene. The extract is dried, filtered and evaporated. The residue is triturated in 4-methyl-2-pentanone. The product is filtered off and crystallized from 4-methyl-2-pentanone, yielding 14.7 parts (78%) of cis-1-{4-[2-(2,4-dichlorophenyl)-2-(1H-imidazol-1ylmethyl)-1,3-dioxolan-4-ylmethoxy]phenyl}-1H-imidazole; mp. 142.9° C.

EXAMPLE XII

Following the procedure of Example XI there are prepared cis-1-{4-[2-(2,4-dichlorophenyl)-2-(1H-imidazol-1-ylmethyl)-1,3-dioxolan-4-ylmethoxy 1]-phenyl}-2-methyl-1H-imidazole dinitrate; mp. 183.8° C. by the reaction of 4-(2-methyl-1H-imidazole-1-yl)phenol monohydrobromide with cis-2-(2,4-dichlorophenyl)-2-(1H-imidazol-1-ylmethyl)-1,3-dioxolan-4-ylmethyl methanesulfonate; and cis-1-{4-[2-(2,4-dichlorophenyl)-2-(1H-imidazol-1-ylmethyl)-1,3-dioxolan-4-ylmethoxy]-phenyl}-2-ethyl-1H-imidazole ethanedioate (1:2); mp. 185.6° C. by the reaction of the latter with 4-(2-ethyl-1H-imidazol-1yl)phenol.

EXAMPLE XIII

A mixture of 4 parts of ethanimidamide hydrochloride, 5 parts of cis N-{4-]2-(2,4-dichlorophenyl)- 2-(1H-imidazol-1-ylmethyl)-1,3-dioxolan-4-ylmethoxy]-phenyl}hydrazinecarboxamide hemihydrate and 4 parts of sodium acetate is melted together in an oil-bath at 160° C. for 30 minutes. The melt is dissolved in trichloromethane. The solution is washed with water, dried, filtered and evaporated. The residue is purified by column-chromatography over silica gel using a mixture of trichloromethane and methanol (95:5 by volume) as eluent. The pure fractions are collected and the eluent is evaporated. The residue is crystallized from 2-propanol, yielding 2 parts (39%) of cis-4-{4-[2-(2,4-dichlorophenyl)-2-(1H-imidazol-1ylmethyl)-1,3-dioxolan-4-ylmethoxy]phenyl}-2,4-dihydro-5-methyl-3H-1,2,4-triazol-3-one; mp. 223.8° C.

EXAMPLE XIV

6 Parts of cis N-{4-[2-(2,4-dichlorophenyl)-2-(1H-imidazol-1-ylmethyl)-1,3-dioxolan-4-ylmethoxy]-phenyl}hydrazinecarboxamide.hemihydrate and 5 parts of methanimidamide acetate are mixed and melted together under IR-radiation. The melt is cooled and dissolved in trichloromethane. The solution is washed with water and treated with activated charcoal. The latter is filtered off and the filtrate is evaporated. The residue is triturated in a mixture of 2-propanol and 1,1'-oxybisethane. The product is filtered off and crystallized from 2-propanol, yielding 3.6 parts (60%) of cis-4-{4-[2-(2,4-dichlorophenyl)-2-(1H-imidazol-1-ylmethyl)-1,3-dioxolan-4-ylmethoxy]phenyl}-2,4-dihydro-3H-1,2,4-triazol-3-one; mp. 212.8° C.

EXAMPLE XV

To a stirred solution of 1.2 parts of 1-bromopropane and 4 parts of cis-4-{4-[2-(2,4-dichlorophenyl)-2-(1H-imidazol-1-ylmethyl)-1,3-dioxolan-4-ylmethoxy]phenyl}-2,4-dihydro-3H-1,2,4-triazol-3-one in 50 parts of dimethylsulfoxide are added 0.32 parts of sodium hydride dispersion 78%. Stirring is continued first for one hour at room temperature and further for one hour at 50° C. The reaction mixture is poured onto water and the product is extracted twice with 1,1'-oxybisethane. The combined extracts are washed with water, dried, filtered and evaporated. The residue is purified by column-chromatography over silica gel using a mixture of trichloromethane and methanol (98:2 by volume) as eluent. The pure fractions are collected and the eluent is evaporated. The residue is crystallized from a mixture of 4-methyl-2-pentanone and 2,2'-oxybispropane, yielding 3 parts (70%) of cis-4-{4[2-(2,4-dichlorophenyl)-2-(1H-imidazol-1-ylmethyl)-1,3-dioxolan-4-ylmethoxy]phenyl}-2,4-dihydro-2-propyl-3H-1,2,4-triazol-3-one; mp. 143.3° C.

EXAMPLE XVI

Following the procedure of Example XV there are prepared cis-4-{4-[2-(2,4-dichlorophenyl)-2-(1H-imidazol-1ylmethyl)-1,3-dioxolan-4-ylmethoxy]phenyl}2,4-dihydro-2-(1-methylethyl)-3H-1,2,4-triazol-3-one; mp. 145.7° C. by the reaction of cis-4-{4-[2-(2,4-dichlorophenyl)-2-(1H-imidazol-1-ylmethyl)-1,3-dioxolan-4-ylmethoxy]phenyl}-2,4-dihydro-3H-1,2,4-triazol-3-one with 2-bromopropane; cis-4-{4-[2-(2,4-dichlorophenyl)-2-(1H-imidazol-1-ylmethyl)-1,3-dioxolan-4-ylmethoxy]phenyl}-2,4-dihydro-2-methyl-3H-1,2,4-triazol-3-one; mp. 144.2° C. by the reaction of the former with iodomethane; and cis-4-{4-[2-(2,4-dichlorophenyl)-2-(1H-imidazol-ylmethyl)-1,3-dioxolan-4-ylmethoxy]phenyl}-2,4-dihydro-5-methyl-2-propyl-3H-1,2,4-triazol-3-one mononitrate; mp. 180.2° C. by the reaction of cis-4-{4-[2-(2,4-diclorophenyl)-2-(1H-imidazol-1-ylmethyl)-1,3-dioxolan-4-ylmethoxy]phenyl}-2,4-dihydro-5-methyl-3H-1,2,4-triazol-3-one with 1-bromopropane.

EXAMPLE XVII

5 Parts of methanimidamide acetate and 5 parts of cis-N-{4-[2-(2,4-dichlorophenyl)-2-(1H-imidazol-1-ylmethyl)-1,3-dioxolan-4-ylmethoxy]phenyl}hydrazinecarbothioamide are mixed intimately in a mortar and then heated for about 30 minutes at 160° C. The reaction mixture is cooled, water is added and the product is extracted with trichloromethane. The extract is dried, filtered and evaporated. The residue is crystallized from 2-propanol, yielding 2.5 parts (50%) of cis-4-{4-[2-(2,4-dichlorophenyl)-2-(1H-imidazol-1ylmethyl)-1,3-dioxolan-4-ylmethoxy]phenyl}-4H-1,2,4-triazol-3-thiol; mp. 235.3° C.

EXAMPLE XVIII

A mixture of 5 parts of cis-4-{4-[2-(2,4-dichlorophenyl)-2-(1H-imidazol-1-ylmethyl)-1,3-dioxolan-4-ylmethoxy]phenyl}-4H-1,2,4-triazole-3-thiol, 5 parts of Raney-nickel catalyst and 200 parts of methanol is stirred and refluxed for one hour. The solution is decanted while hot. 450 Parts of trichloromethane are added. The organic phase is dried, filtered and evaporated. The residue is crystallized from 4-methyl-2-pentanone. The product is filtered off and dried, yielding 2 parts (42%) of cis-4-{4-[2-(2,4-dichlorophenyl)-2-(1H-imidazol-1-ylmethyl)-1,3-dioxolan-4-ylmethoxy]phenyl}-4H-1,2,4-triazole; mp. 153.4° C.

EXAMPLE XIX

Following the procedure of Example XI and using equivalent amounts of the appropriate starting materials the following compounds are still obtained:

trans-1-{4-[2,4-dichlorophenyl)-2-(1H-imidazol-1-ylmethyl)-1,3-dioxolan-4-ylmethoxy]phenyl}-1H-imidazole;

trans-1-{4-[2-(2,4-dichlorophenyl)-2-(1H-imidazol-1-ylmethyl)-1,3-dioxolan-4-ylmethoxy]phenyl}-1H-1,2,4-triazole;

trans-1-{4-[2-(2,4-dichlorophenyl)-2-(1H-imidazol-1-ylmethyl)-1,3-dioxolan-4-ylmethoxy]phenyl}-1H-pyrazole;

1-{4-[2-(4-chlorophenyl)-2-(1H-imidazol-1-ylmethyl)-1,3-dioxolan-4-ylmethoxy]phenyl}-1H-imidazole;

1-{4-[2-(4-bromophenyl)-2-(1H-imidazol-1-ylmethyl)-1,3-dioxolan-4-ylmethoxy]phenyl}-1H-imidazole;

1-{4-[2-(4-fluorophenyl)-2-(1H-imidazol-1-ylmethyl)-1,3-dioxolan-4-ylmethoxy]phenyl}-1H-imidazole;

1-{4-[2-(2,6-dichlorophenyl)-2-(1H-imidazol-1-ylmethyl)-1,3-dioxolan-4-ylmethoxy]phenyl}-1H-imidazole;

1-{4-[2-(1H-imidazol-1-ylmethyl)-2-(4-methylphenyl)-1,3-dioxolan-4-ylmethoxy]phenyl}-1H-imidazole;

1-{4-[2-(1H-imidazol-1-ylmethyl)-2-(4-methoxyphenyl)-1,3-dioxolan-4-ylmethoxy]phenyl}-1H-imidazole;

1-{4-[2-(1H-imidazol-1-ylmethyl)-2-(2-methyl-4-chlorophenyl)-1,3-dioxolan-4-ylmethoxy]phenyl}-1H-imidazole;

1-{4-[2-(4-chlorophenyl)-2-(1H-imidazol-1-ylmethyl)-1,3-dioxolan-4-ylmethoxy]phenyl}-1H-pyrazole;

1-{4-[2-(1H-imidazol-1-ylmethyl)-2-(4-methylphenyl)-1,3-dioxolan-4-ylmethoxy]phenyl}-1H-pyrazole;

1-{4-[2-(1H-imidazol-1-ylmethyl)-2-(4-methoxyphenyl)-1,3-dioxolan-4-ylmethoxy]phenyl}-1H-pyrazole;

1-{4-[2-(4-chlorophenyl)-2-(1H-imidazol-1-ylmethyl)-1,3-dioxolan-4-ylmethoxy]phenyl}-1H-1,2,4-triazole;

1-{4-[2-(1H-imidazol-1-ylmethyl)-2-(4-methylphenyl)-1,3-dioxolan-4-ylmethoxy]phenyl}-1H-1,2,4-triazole; and 1-{4-[2-(1H-imidazol-1-ylmethyl)-2-(4-methoxyphenyl)-1,3-dioxolan-4-ylmethoxy]phenyl}-1H-1,2,4-triazole.

EXAMPLE XX

A mixture of 8.7 parts of (4-methoxyphenyl)hydrazine hydrochloride, 8.1 parts of 1-phenyl-1,3-butanedione, 7 parts of potassium carbonate and 160 parts of ethanol is stirred and refluxed for 20 hours. The reaction mixture is cooled and poured onto water. The product is extracted twice with 2,2'-oxybispropane. The combined extracts are washed with water, dried, filtered and evaporated. The residue is crystallized twice from petroleumether. The product is filtered off and dried, yielding 7 parts (53%) of 1-(4-methoxyphenyl)-3-methyl-5phenyl-1H-pyrazole; mp. 110° C.

EXAMPLE XXI

Following the procedure of Example XX and using an equivalent amount of respectively 2,2,6,6-tetramethyl-3,5-heptanedione, 2,4-pentanedione or 1,3-diphenyl-1,3-propanedione in place of the 1-phenyl-1,3-butanedione used therein the following pyrazoles are obtained:
3,5-bis(1,1-dimethylethyl)-1-(4-methoxyphenyl)-1H-pyrazole; mp. 122.6° C;
1-(4-methoxyphenyl)-3,5-dimethyl-1H-pyrazole monohydrochloride; mp. 131°–136° C; and
1-(4-methoxyphenyl)-3,5-dimethyl-1H-pyrazole; mp. 119.4° C.

EXAMPLE XXII

A mixture of 17.5 parts of 2-amino-1-phenylethanone hydrochloride, 16.5 parts of 1-isothiocyanato-4-methoxybenzene, 10 parts of sodium hydrogen carbonate and 200 parts of 2-propanol is stirred first for 30 minutes at room temperature and further for 2 hours at reflux temperature. The reaction mixture is poured onto 500 parts of water. The product is filtered off and stirred and refluxed for 1 hour with 240 parts of hydrochloric acid solution 10%. After cooling, the product is filtered off, washed with water and 2-propanol, and dried, yielding 25.3 parts (90%) of 1-(4-methoxyphenyl)-5-phenyl-1H-imidazole-2-thiol; m.p. 267.4° C.

EXAMPLE XXIII

A mixture of 12 parts of 1-(4-methoxyphenyl)-5-phenyl-1H-imidazole-2-thiol, 10 parts of Raney-nickel catalyst, 160 parts of ethanol, 180 parts of ethyl acetate and 36 parts of ammonium hydroxide is stirred and refluxed overnight. The solution is decanted and the residual Randy-nickel is boiled again in a mixture of 160 parts of ethanol and 180 parts of ethyl acetate. The solvent is decanted. The combined ethanol/ethyl acetate phases are evaporated. The residue is crystallized from a mixture of 2-propanol and water. The product is filtered off and dried, yielding 6.5 parts (61%) of 1-(4-methoxyphenyl)-5-phenyl-1H-imidazole; m.p. 105.7° C.

EXAMPLE XXIV

To a stirred solution of 17 parts of 1-(4-methoxyphenyl)-1H-imidazole-2-thiol and 10.15 parts of bromoethane in 200 parts of dimethylsulfoxide are added 2.9 parts of sodium hydride dispersion 78%. The whole is stirred for 2 hours at room temperature. The reaction mixture is poured onto water and the product is extracted twice with 2,2'-oxybispropane. The combined extracts are washed with water, dried, filtered and acidified with 2-propanol, previously saturated with gaseous hydrogen chloride. The formed hydrochloride salt is filtered off and crystallized from 2-propanol. The product is filtered off and dried, yielding 18 parts (81%) of 2-(ethylthio)-1-(4-methoxyphenyl)-1H-imidazole monohydrochloride; mp. 175° C.

EXAMPLE XXV

Following the procedure of Example XXIV and using an equivalent amount of an appropriate bromoalkane in place of the bromoethane used therein, there are prepared:

1-(4-methoxyphenyl)-2-(propylthio)-1H-imidazole monohydrochloride; mp. 136.8° C; and
1-(4-methoxyphenyl)-2-[(1-methylethyl)thio ]-1H-imidazole monohydrochloride; mp. 172.6° C.

EXAMPLE XXVI

To a stirred solution of 11 parts of 1-(4-methoxyphenyl)-1H-imidazole-2-thiol in 100 parts of dimethylsulfoxide are added 1.6 parts of sodium hydride dispersion 78%. After stirring for one hour at room temperature, 6.65 parts of dimethyl sulfate are added and the whole is further stirred for one hour at room temperature. The reaction mixture is poured onto water and the product is extracted twice with 1,1'-oxybisethane. The combined extracts are washed with water, dried, filtered and the filtrate is acidified with 2-propanol, previously saturated with gaseous hydrogen chloride. The formed hydrochloride salt is filtered off and crystallized from 2-propanol, yielding 7.8 parts (60%) of 1-(4-methoxyphenyl)-2-(methylthio)-1H-imidazole monohydrochloride; mp. 178° C.

EXAMPLE XXVII

To a stirred solution of 2.2 parts of 1(4-methoxyphenyl)-5-methyl-1-H-imidazole-2-thiol and 0.8 parts of sodium hydroxide in 80 parts of methanol are added 1.33 parts of dimethyl sulfate. The whole is stirred for one hour at room temperature and poured onto water. The product is extracted with 1,1'-oxybisethane. The extract is dried, filtered and the filtrate is acidified with 2-propanol, previously saturated with gaseous hydrogen chloride. The formed hydrochloride salt is filtered off and crystallized from 2-propanol, yielding 1.8 parts (66%) of 1(4-methoxyphenyl)-5-methyl-2-(methylthio)-1H-imidazole monohydrochloride; mp. 218.3° C.

EXAMPLE XXVIII

Following the procedure of Example XXVII there is prepared 1-(4-methoxyphenyl)-2-(methylthio)-5-phenyl-1H-imidazole; mp 159° C., by the reaction of 1-(4-methoxyphenyl)-5-phenyl-1-H-imidazole-2-thiol with dimethyl sulfate.

EXAMPLE XXIX

A mixture of 13.5 parts of N-(4-methoxyphenyl)-hydrazinecarbothioamide, 15 parts of ethanimidamide hydrochloride, 15 parts of sodium acetate and 120 parts of 1-butanol is stirred and refluxed for 1 hour. The reaction mixture is cooled, 100 parts of water are added, followed by the addition of 140 parts of petroleumether. The precipitated product is filtered off and dried, yielding 12.5 parts (83%) of 4(4-methoxyphenyl)-5-methyl-4H-1,2,4-triazole-3-thiol; m.p. 214.2° C.

EXAMPLE XXX

Following the procedure of Example XXIX and using an equivalent amount of an appropriate alkanimidamide hydrochloride in place of the ethanimidamide used therein there are prepared:
5-ethyl-4-(4-methoxyphenyl)-4H-1,2,4--triazole-3-thiol; mp. 191.5° C. and
4-(4-methoxyphenyl)-5-propyl-4H-1,2,4-triazole-3-thiol; mp. 165.4° C.

EXAMPLE XXXI

A mixture of 10.5 parts of 4-(4-methoxyphenyl)-5-methyl-4H-1,2,4-triazole-3-thiol, 10 parts of Raney-nickel catalyst, 18 parts of ammonium hydroxide and 200 parts of methanol is stirred and refluxed for 4 hours. The reaction mixture is decanted while hot and the Raney-nickel catalyst is boiled in 160 parts of methanol. The latter is decanted and the combined methanol-phases are evaporated. The residue is crystallized from a mixture of 4-methyl-2-pentanone and 2,2'-oxybispropane. The product is filtered off and dried, yielding 4.2 parts of 4-(4-methoxyphenyl)-3-methyl-4H-1,2,4-triazole; mp. 111.9° C.

EXAMPLE XXXII

Following the procedure of Example XXXI the following 4-(4-methoxyphenyl)-4H-1,2,4-triazoles are obtained by desulfurizing the corresponding 4-(4-methoxyphenyl)-4H-1,2,4-triazole-3-thiols:
3-ethyl-4-(4-methoxyphenyl)-4H-1,2,4-triazole monohydrochloride; mp. 221.2° C; and 4-(4-methoxyphenyl)-3-propyl-4H-1,2,4-triazole monohydrochloride.

EXAMPLE XXXIII

To a stirred solution of 2.1 parts of 4-(4-methoxyphenyl)-4H-1,2,4-triazole-3-thiol and 0.8 parts of sodium hydroxide in 40 parts of methanol are added 1.33 parts of dimethyl sulfate and stirring is continued for 1 hour at room temperature. The reaction mixture is poured onto water and the product is extracted three times with dichloromethane. The combined extracts are washed with a saturated sodium chloride solution, dried, filtered and evaporated. The residue is converted into the hydrochloride salt in 2-propanol and 2,2'-oxybispropane. The salt is filtered off and crystallized from 2-propanol. The product is filtered off and dried, yielding 1.8 parts (70%) of 4-(4-methoxyphenyl)-3-(methylthio)-4H-1,2,4-triazole monohydrochloride; mp. 171.5° C.

EXAMPLE XXXIV

Following the procedure of Example XXXIII there is prepared 4-(4-methoxyphenyl)-3-methyl-5-(methylthio)-4H-1,2,4-triazole monohydrochloride; mp. 165.1° C., by the reaction of 4-(4-methoxyphenyl)-5-methyl-4H-1,2,4-triazole-3-thiol with dimethyl sulfate.

EXAMPLE XXXV

To a stirred solution of 35.7 parts of 4-(4-methoxyphenyl)-3-(methylthio)-4H-1,2,4-triazole monohydrochloride in 100 parts of acetic acid and 300 parts of water are added portionwise 44 parts of potassium permanganate while the temperature has been kept at about 30° C. Upon completion, stirring is continued for 2 hours at room temperature. The reaction mixture is decoloured with a sodium sulfite solution and neutralized with sodium hydrogen carbonate. The whole is filtered and the filter-cake is boiled first twice in 320 parts of methanol and then twice in 360 parts of ethyl acetate, while at each time, the mixture is filtered. The combined filtrates are evaporated and the residue is triturated in 200 parts of water. The product is filtered off, washed with water and with 2-propanol, and dried, yielding 28 parts (80%) of 4-(4-methoxyphenyl)-3-(methylsulfonyl)-4H-1,2,4-triazole; mp. 191.1° C.

EXAMPLE XXXVI

A mixture of 17 parts of (4-methoxyphenyl)hydrazine hydrochloride, 16.3 parts of benzoyl isothiocyanate, 10 parts of N,N-diethylethanamine and 130 parts of dichloromethane is stirred for 1 hour at room temperature. The mixture is washed with water and the solvent is evaporated. Then there are added 4.5 parts of sodium hydroxide solution 50% and 80 parts of ethanol to the residue and the whole is stirred and refluxed for 30 minutes. The mixture is neutralized with concentrated hydrochloric acid and diluted with water. The precipitated product is filtered off and crystallized from 1-butanol, yielding 13 parts (46%) of 1-(4-methoxyphenyl)-5-phenyl-1H-1,2,4-triazole-3-thiol; mp. 260° C.

EXAMPLE XXXVII

A mixture of 10 parts of 2-(4-methoxyphenyl)-hydrazinecarbothioamide, 10.6 parts of methanimidamide acetate and 80 parts of 1-butanol is stirred and refluxed for 1 hour. After cooling, water and 2,2'-oxybispropane are added, whereupon the product is precipitated. It is filtered off and dried, yielding 7.6 parts (73%) of 1-(4-methoxyphenyl)-1H-1,2,4-triazole-3-thiol.

EXAMPLE XXXVIII

A mixture of 17.5 parts of 2-(4-methoxyphenyl)hydrazinecarbothioamide, 10 parts of acetic acid anhydride and 90 parts of dimethylbenzene is stirred and refluxed for one hour. The reaction mixture is allowed to cool to room temperature and 2,2'-oxybispropane and water are added. The precipitated product is filtered off and dried, yielding 14.5 parts (89%) of acetic acid 2-(aminothioxomethyl)-1-(4-methoxyphenyl)hydrazide.

A mixture of 14.5 parts of acetic acid 2-(aminothioxomethyl)-1-(4-methoxyphenyl)hydrazide, 5 parts of sodium hydroxide and 80 parts of methanol is stirred and refluxed for 30 minutes. The reaction mixture is cooled and water is added. The whole is adjusted to pH 5 with a hydrochloric acid solution. The precipitated product is filtered off and dried, yielding 12.3 parts (91%) of 1-(4-methoxyphenyl)-5-methyl-1H-1,2,4-triazole-3-thiol.

EXAMPLE XXXIX

Following the procedure of Example XXXVIII and using an equivalent amount of propanoic acid anhydride in place of the acetic acid anhydride used therein there is prepared 5-ethyl-1-(4-methoxyphenyl)-1H-1,2,4-triazole-3-thiol.

EXAMPLE XL

A mixture of 4.5 parts of 1-(4-methoxyphenyl)-5-methyl-1H-1,2,4-triazole-3-thiol, 16 parts of Raney-nickel catalyst, 80 parts of methanol and 27 parts of ammonium hydroxide is stirred and refluxed overnight. The reaction mixture is filtered and the filtrate is evaporated. The residue is converted into the hydrobromide salt with a hydrobromic acid solution 48% in glacial acetic acid. The solvent is evaporated and the residue is triturated in 2-propanone. The salt is filtered off and dried, yielding 4.9 parts (90%) of 1-(4-methoxyphenyl)-5-methyl-1H-1,2,4-triazole monohydrobromide; mp. 185.8° C.

EXAMPLE XLI

Following the procedure of Example XL the following 1H-1,2,4-triazole and acid addition salts thereof are obtained by desulfurizing the corresponding 1H-1,2,4-triazole-3-thiols:
5-ethyl-1-(4-methoxyphenyl)-1H-1,2,4-triazole ethanedioate (1:1); and 1-(4-methoxyphenyl)-5-phenyl-1H-1,2,4-triazole; mp. 98.1° C.

EXAMPLE XLII

A mixture of 8 parts of 1-(4-methoxyphenyl)-1H-1,2,4-triazole-3-thiol, 3.1 parts of sodium hydroxide and 40 parts of methanol is stirred for 30 minutes at room temperature. Then there are added 4.9 parts of dimethyl sulfate and stirring at room temperature is continued for 3 hours. Water is added to the reaction mixture and the product is extracted twice with 1,1'-oxybisethane. The combined extracts are dried, filtered and evaporated. The residue is purified by column-chromatography over silica gel using trichloromethane as eluent. The pure fractions are collected and the eluent is evaporated. The residue is crystallized from 2,2'-oxybispropane, yielding 5.6 parts (65%) of 1-(4-methoxyphenyl)-3-(methylthio)-1H-1,2,4-triazole; mp. 54.9° C.

EXAMPLE XLIII

Following the procedure of Example XLII there is prepared 1-(4-methoxyphenyl)-5-methyl-3-(methylthio)-1H-1,2,4-triazole monohydrochloride; mp. 179.3° C., by the reaction of 1-(4-methoxyphenyl)-5-methyl-1H-1,2,4-triazole-3-thiol with dimethyl sulfate.

EXAMPLE XLIV

A mixture of 6 parts of 1-(4-methoxyphenyl)-5-methyl-1H-1,2,4-triazole-3-thiol, 2.2 parts of sodium hydroxide and 60 parts of methanol is stirred for 30 minutes at room temperature. Then there are added 4.4 parts of bromoethane and stirring is continued for 3 hours. Water is added and the product is extracted with 2,2'-oxybispropane. The extract is dried, filtered and evaporated. The residue is converted into the hydrochloride salt in 4-methyl-2-pentanone and 2,2'-oxybispropane. The salt is filtered off and crystallized from a mixture of 2-propanol and 2,2'-oxybispropane, yielding 3 parts (38%) of 3-(ethylthio)-1-(4-methoxyphenyl)-5-methyl-1H-1,2,4-triazole monohydrochloride; mp. 149.2° C.

EXAMPLE XLV

Following the procedure of Example XLIV and using equivalent amounts of the appropriate starting materials there are prepared:
3-(ethylthio)-1-(4-methoxyphenyl)-1H-1,2,4-triazole as a residue; and
5-ethyl-3-(ethylthio)-1-(4-methoxyphenyl)-1H-1,2,4-triazole monohydrochloride; mp. 123.4° C.

EXAMPLE XLVI

A mixture of 14 parts of 2-(ethylthio)-1-(4-methylphenyl)-1H-imidazole monohydrochloride and 113 parts of hydrobromic acid solution 48% in glacial acetic acid is stirred and refluxed for 3 hours. The reaction mixture is evaporated and the residue is dissolved in water. The solution is neutralized with sodium hydrogen carbonate. The precipitated product is filtered off and crystallized from 2-propanol, yielding 8.3 parts (72.5%) of 4-[2-(ethylthio)-1H-imidazol-1-yl]phenol; mp. 165.2° C.

EXAMPLE XLVII

Following the procedure of Example XLVI the following phenols are prepared starting from the corresponding methoxy substituted compounds:
4-[2-(methylthio)-1H-imidazol-1-yl]phenol; mp. 204° C.;
4-[2-(propylthio)-1H-imidazol-1-yl]phenol; mp. 118.1° C.;
4-{2-[(1-methylethyl)thio]-1H-imidazol-1-yl}phenol; mp. 162.9° C.;
4-(5-methyl-1H-imidazol-1-yl)phenol; mp. 245.2° C.;
4-[5-methyl-2-(methylthio)-1H-imidazol-1-yl]phenol; mp. 255.5° C.;
4-[2-(methylthio)-5-phenyl-1H-imidazol-1-yl]phenol; mp. 236.3° C.;
4-(5-phenyl-1H-imidazol-1-yl)phenol; mp. 301°-310° C.;
4-(3,5-dimethyl-1H-pyrazol-1-yl)phenol; mp. 163.3° C.;
4-(3,5-diphenyl-1H-pyrazol-1-yl)phenol 2-propanolate (2:1); mp. 215.6° C.;
4-[3,5-bis(1,1-dimethylethyl)-1H-pyrazol-1-yl]phenol; mp. 268.7° C.,
4-(3-methyl-5-phenyl-1H-pyrazol-1-yl)phenol; mp. 209.7° C.;
4-(3-methyl-1H-pyrazol-1-yl)phenol;
4-[3-(ethylthio)-1H-1,2,4-triazol-1-yl]phenol; mp. 166.6° C.;
4-[3-(methylthio)-1H-1,2,4-triazol-1-yl]phenol; mp. 170° C.;
4-[5-ethyl-3-(ethylthio)-1H-1,2,4-triazol-1-yl]phenol monohydrobromide; mp. 171.2° C.;
4-[5-methyl-3-(methylthio)-1H-1,2,4-triazol-1-yl]phenol monohydrobromide; mp. 239.2° C.;
4-[3-(ethylthio)-5-methyl-1H-1,2,4-triazol-1-yl]phenol monohydrobromide;
4-(5-phenyl-1H-1,2,4-triazol-1-yl)phenol monohydrobromide; mp. 261.6° C.;
4-(5-methyl-1H-1,2,4-triazol-1-yl)phenol monohydrobromide; mp. 262.4° C.;
4-(5-ethyl-1H-1,2,4-triazol-1-yl)phenol; mp. 136.7° C.;
4-(3-methyl-4H-1,2,4-triazol-4-yl)phenol; mp. 289.5° C.;
4-(3-ethyl-4H-1,2,4-triazol-4-yl)phenol; mp. 239.9° C.;
4-[3-methyl-5-(methylthio)-4H-1,2,4-triazol-4-yl]phenol; mp. 261.3° C.;
4-[3-(methylsulfonyl)-4H-1,2,4-triazol-4-yl]phenol; mp. 211.5° C.;
4-(3-propyl-4H-1,2,4-triazol-4-yl)phenol; and
4-[3-(methylthio)-4H-1,2,4-triazol-4-yl]phenol; mp. 176.2° C.

EXAMPLE XLVIII

A mixture of 174 parts of 2-bromo-1-(3-chlorophenyl)ethanone, 81 parts of 1,2,3-propanetriol, 7.4 parts of 4-methylbenzenesulfonic acid, 94 parts of 1-butanol and 528 parts of benzene is stirred and refluxed for 20 hours with water-separator. The reaction mixture is poured onto a diluent sodium hydroxide solution and the layers are separated. The aqueous phase is extracted twice with methylbenzene. The combined organic phases are washed twice with water, dried, filtered and evaporated, yielding 238 parts of cis+trans-2-(bromomethyl)-2-(3-chlorophenyl)-1,3-dioxolane-4-methanol as a residue.

238 Parts of cis+trans-2-(bromomethyl)-2-(3-chlorophenyl)-1,3-dioxolane-4-methanol are dissolved in a mixture of 144 parts of pyridine and 1135 parts of trichloromethane and the solution is cooled to about 5° C. Then there are added dropwise 149 parts of benzoyl chloride at a temperature below 10° C. Upon completion, stirring is continued for 2 hours at room temperature. The reaction mixture is poured onto water and the layers are separated. The aqueous phase is extracted twice with trichloromethane. The combined extracts are washed twice with water, dried, filtered and evaporated. The residue is stirred for a few hours in hexane.

The precipitated product is filtered off and dried at the air, yielding 128 parts of cis+trans-[2-(bromomethyl)-2-(3-chlorophenyl)-1,3-dioxolan-4-ylmethyl] benzoate.

A mixture of 26 parts of 1H-imidazole and 68.5 parts of sodium methanolate solution 30% is stirred and refluxed for 15 minutes. 90 Parts of N,N-dimethylformamide are added and the methanol is distilled off till an internal temperature of 130° C. Then there is added dropwise a solution of 102.5 parts of cis+trans-[2-(bromomethyl)-2-(3-chlorophenyl)-1,3-dioxolan-4-ylmethyl] benzoate in 225 parts of N,N-dimethylformamide. Upon completion, stirring is continued for 3 hours at reflux. The reaction mixture is cooled, water is added and the product is extracted three times with 4-methyl-2-pentanone. The combined extracts are washed twice with water, dried, filtered and evaporated, yielding 43 parts of cis+trans-[2-(3-chlorophenyl)-2-(1H-imidazol-1-ylmethyl)-1,3-dioxolan-4-ylmethyl] benzoate as a residue.

A mixture of 45 parts of cis+trans-[2(3-chlorophenyl)-2-(1H-imidazol-1-ylmethyl)-1,3-dioxolan-4-ylmethyl] benzoate, 36 parts of sodium hydroxide solution 50%, 600 parts of 1,4-dioxane and 200 parts of water is stirred and refluxed for 1 hour. The reaction mixture is cooled and poured onto water. Trichloromethane is added and the layers are separated. The organic phase is washed with water, dried, filtered and evaporated. The residue is converted into the hydrochloride salt in 2-propanone and 2-propanol. After stirring for 2 hours in an ice-bath, the salt is filtered off and dried, yielding 14 parts of cis+trans-2-(3-chlorophenyl)-2-(1H-imidazol-1-ylmethyl)-1,3-dioxolane-4-methanol monohydrochloride; mp. 198.3° C.

A mixture of 68 parts of cis+trans-2-(3-chlorophenyl)-2-(1H-imidazol-1-ylmethyl)-1,3-dioxolane-4-methanol and 570 parts of pyridine is cooled to 0° C. The ice-bath is taken away and 26.3 parts of methanesulfonyl chloride are added dropwise (exothermic reaction: temp. rises to 20° C.). Upon completion, stirring is continued for 3 hours at room temperature. The reaction mixture is poured onto water and the product is extracted with trichloromethane. The extract is dried, filtered and evaporated. The residue is converted into the hydrochloride salt in 2-propanone and 2-propanol. The salt is filtered off and crystallized from 2-propanol, yielding 32 parts of [2-(3-chlorophenyl)-2-(1H-imidazol-1-ylmethyl)-1,3-dioxolan-4-ylmethyl] methanesulfonate monohydrochloride.

EXAMPLE IL

Following the procedure of Example XLVIII and using equivalent amounts of the appropriate starting materials there is prepared:
[2-(1H-imidazol-1-ylmethyl)-2-(4-methoxyphenyl)-1,3-dioxolan-4-ylmethyl] methanesulfonate.

EXAMPLE L

A mixture of 1.6 parts of 1H-1,2,4-triazole, 54 parts of N,N-dimethylformamide and 45 parts of benzene is stirred and refluxed for 2 hours. After cooling, 0.78 parts of sodium hydride dispersion 78% are added and the whole is stirred for 30 minutes at room temperature. Then there are added 8.9 parts of cis-2-(bromomethyl)-2-(2,4-dichlorophenyl)-1,3-dioxolan-4-ylmethyl benzoate and stirring is continued overnight at 150° C. The reaction mixture is cooled and poured onto water. The product is extracted three times with benzene. The combined extracts are washed twice with water, dried, filtered and evaporated, yielding 8.5 parts of cis-[2-(2,4-dichlorophenyl)-2-(1H-1,2,4-triazol-1-ylmethyl)-1,3-dioxolan-4-ylmethyl] benzoate as a residue.

A mixture of 289 parts of cis-[2-(2,4-dichlorophenyl)-2-(1H-1,2,4-triazol-1-ylmethyl)-1,3-dioxolan-4-ylmethyl] benzoate, 200 parts of sodium hydroxide solution 50%, 1500 parts of 1,4-dioxane and 300 parts of water is stirred and refluxed for 2 hours. The reaction mixture is cooled and poured onto water. The product is extracted with dichloromethane. The extract is washed with water, dried, filtered and evaporated. The residue is purified by column-chromatography over silica gel using a mixture of trichloromethane and methanol (95:5 by volume) as eluent. The first fraction is collected and the eluent is evaporated, yielding 89 parts of cis-2-(2,4-dichlorophenyl)-2-(1H-1,2,4-triazol-1-ylmethyl)-1,3-dioxolane-4-methanol; mp. 138.2° C.

A mixture of 30.6 parts of cis-2-(2,4-dichlorophenyl)-2-(1H-1,2,4-triazol-1-ylmethyl)-1,3-dioxolane-4-methanol and 75 parts of pyridine is stirred at room temperature and there are added dropwise 17.2 parts of methanesulfonyl chloride. Upon completion, stirring is continued overnight at room temperature. The reaction mixture is poured onto ice-water and the product is extracted twice with dichloromethane. The combined extracts are washed twice with a diluted hydrochloric acid solution and twice with water, dried, filtered and evaporated. The residue is purified by column-chromatography over silica gel using a mixture of trichloromethane and methanol (95:5 by volume) as eluent. The first fraction is collected and the eluent is evaporated, yielding 21 parts of cis-[2-(2,4-dichlorophenyl)-2-(1H-1,2,4-triazol-1-ylmethyl)-1,3-dioxolan-4-ylmethyl] methanesulfonate; mp. 98° C.

EXAMPLE LI

Following the procedure of Example VIII and using equivalent amounts of the appropriate starting materials the following compounds of formula I having the cis-configuration and acid addition salts thereof are prepared:

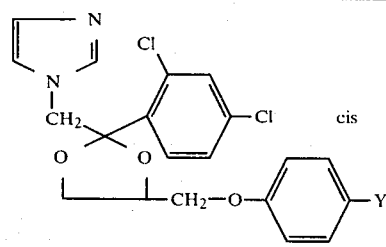

| Y | Salt or base form | m.p. °C. |
|---|---|---|
| ![triazole with CH3] -N⟩=N with CH3 | 2HNO3 | 191.9 |
| ![triazole with CH2CH3] -N⟩=N with CH2—CH3 | 2HNO3 | 166.4 |

-continued

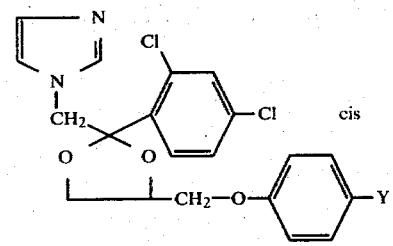

cis

| Y | Salt or base form | m.p. °C. |
|---|---|---|
| -N(=N-CH=N-ring with CH2-CH2-CH3) | 2HNO3 | 172.3 |
| -N(=N-CH=N-ring with S-CH3) | base | 135.4 |
| -N(=N-CH=N-ring with S-CH2-CH3) | 2HNO3 | 156.9 |
| -N(=N-CH=N-ring with S-CH3) | 2HNO3 | 137.8 |
| -N(=N-CH=N-ring with S-CH2-CH2-CH3) | 2HNO3 | 148.6 |
| -N(=N-CH=N-ring with S-CH(CH3)2) | 2HNO3 | 143.7 |
| -N(CH3-C=N-ring with S-CH3) | 2HNO3 | 166.6 |
| -N(CH3-C=N-ring with CH=N) | 2HNO3 | 192.1 |
| -N-N=C(S-CH3)-N=CH- | 2HNO3 | 152.2 |

-continued

| Y | Salt or base form | m.p. °C. |
|---|---|---|
| -N=C(phenyl)-S-CH3 | base | 160.1 |
| -N-N=C(CH2-CH3)-S-CH2-CH3 | HNO3 | 161.4 |
| -N-N=C(phenyl)-CH= with S-CH2-CH3 | 2HNO3 | 164.9 |
| -N-N=C(S-CH2-CH3)-N=CH- | HNO3 | 157.2 |
| -N-N=C(phenyl)-CH=C(phenyl)- | base | 138.3 |
| -N-N=C(S-CH2-CH3)-C(CH3)= | base | 167.1 |
| -N-N=C(C(CH3)3)-CH=C(C(CH3)3)- | base | 192.1 |

-continued

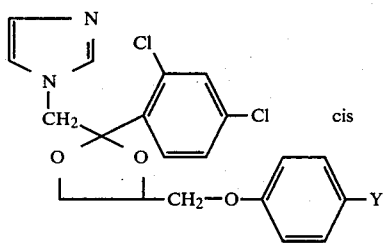

| Y | Salt or base form | m.p. °C. |
|---|---|---|
| 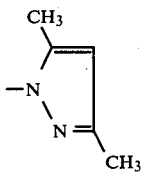 | 2HCl | 196.2 |
| 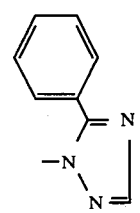 | HNO$_3$ · H$_2$O | 162.1 |
| 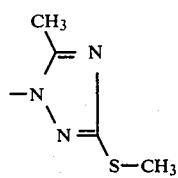 | HNO$_3$ | 162.3 |
| 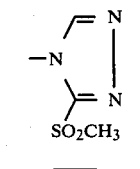 | base ½ H$_2$O | 123.5 |
| 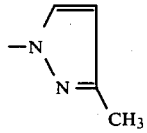 | HNO$_3$ | 187.3 |
| 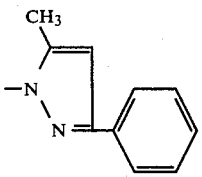 | HCl | 209.9 |
| 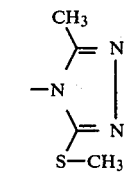 | 2HNO$_3$ | 151.3 |
| 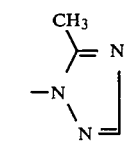 | 2HNO$_3$ | 157 |

-continued

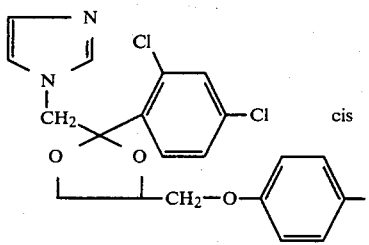

| Y | Salt or base form | m.p. °C. |
|---|---|---|
|  | base H$_2$O | 126 |
|  | 2(COOH)$_2$ | 148.7 |
|  | 2HNO$_3$ | 177.4 |

EXAMPLE LII

Following the procedure of Example VIII and using equivalent amounts of the appropriate starting materials the following compounds of formula I and acid addition salts thereof are still prepared:

cis or trans-1-4-{[2-(3-chlorophenyl)-2-(1H-imidazol-1-ylmethyl)-1,3-dioxolan-4-ylmethoxy]phenyl}-1H-imidazole ethanedioate (1:2); mp. 175.8° C.;

cis-1-{4-[2-(1H-imidazol-1-ylmethyl)-2-(4-methoxyphenyl)-1,3-dioxolan-4-ylmethoxy]-phenyl}-1H-imidazole; mp. 120.4° C.;

cis-1-{3-[2-(2,4-dichlorophenyl)-2-(1H-imidazol-1-ylmethyl)-1,3-dioxolan-4-ylmethoxy]phenyl}-1H-imidazole ethanedioate (1:2); mp. 132.1° C.; and cis-1-{2-[2-(2,4-dichlorophenyl)-2-(1H-imidazol-1-ylmethyl)-1,3-dioxolan-4-ylmethoxy]phenyl}-1H-imidazole ethanedioate (1:2); mp. 172.4° C.

EXAMPLE LIII

To a stirred and cooled (ice-bath) solution of 4 parts of cis-4-{4-[2-(2,4-dichlorophenyl)-2-(1H-imidazol-1-ylmethyl)-1,3-dioxolan-4-ylmethoxy]phenyl}-3-(methylthio)-4H-1,2,4-triazole in 130 parts of dichloromethane are added 1.5 parts of 3-chlorobenzeneperoxoic acid and stirring is continued for 2 hours. The reaction mixture is washed with a sodium hydrogen carbonate solution, dried, filtered and evaporated. The residue is purified by column-chromatography over silica gel using a mixture of trichloromethane and methanol (98:2 by volume) as eluent. The pure fractions are collected and the eluent is evaporated. The residue is converted into the ethanedioate salt in 2-propanol. The salt is filtered off and crystallized from absolute ethanol, yielding 2.7 parts (52%) of cis-4-{4-[2-(2,4-dichlorophenyl)-2-(1H-imidazol-1-ylmethyl)-1,3-dioxolan-4-ylmethoxy]- phenyl}-3-(methylsulfinyl)-4H-1,2,4-triazole ethanedioate (2:3); mp. 142.7° C.

EXAMPLE LIV

Following the procedure of Example LIII there is prepared cis-4-{4-[2-(2,4-dichlorophenyl)-2-(1H-imidazol-1-ylmethyl)-1,3-dioxolan-4-ylmethoxy]-phenyl}-3-methyl-5-(methylsulfinyl)-4H-1,2,4-triazole ethanedioate (1:1).2-propanolate (2:1); mp. 116.4° C. by the reaction of cis-4-{4-[2-(2,4-dichlorophenyl)-2-(1H-imidazol-1-ylmethyl)-1,3-dioxolan-4-ylmethoxy]-phenyl}-3-methyl-5-(methylthio)-4H-1,2,4-triazole with 3-chlorobenzeneperoxoic acid.

EXAMPLE LV

To a stirred solution of 1.35 parts of 1-bromopropane and 5 parts of cis-4-{4-[2-(2,4-dichlorophenyl)-2-(1H-imidazol-1-ylmethyl)-1,3-dioxolan-4-ylmethoxy]-phenyl}-4H-1,2,4-triazole-3-thiol in 100 parts of dimethylsulfoxide are added 0.32 parts of sodium hydride dispersion 78%. The whole is stirred for 3 hours at room temperature. The reaction mixture is poured onto water and the product is extracted twice with trichloromethane. The combined extracts are washed with water, dried, filtered and evaporated. The residue is purified by column-chromatography over silica gel using a mixture of trichloromethane and methanol (98:2 by volume) as eluent. The pure fractions are collected and the eluent is evaporated. The residue is converted into the ethanedioate salt in 2-propanol and 2,2'-oxybispropane. The salt is filtered off and crystallized from 2-propanone, yielding 3.1 parts (42%) of cis-4-{4-[2-(2,4-dichlorophenyl)-2-(1H-imidazol-1-ylmethyl)-1,3dioxolan-4-ylmethoxy]phenyl}-3-(propylthio)-4H-1,2,4-triazole ethanedioate (1:2); mp. 146.9° C.

EXAMPLE LVI

Following the procedure of Example LV there is prepared cis-4-{4-[2-(2,4-dichlorophenyl)-2-(1H-imidazol-1-ylmethyl)-1,3-dioxolan-4-ylmethoxy]-phenyl}3-[(1-methylethyl)thio]-4H-1,2,4-triazole ethanedioate (1:2); mp. 140.2° C. by the reaction of cis-4-{4-[2-(2,4-dichlorophenyl)-2-(1H-imidazol-1-ylmethyl)-1,3-dioxolan-4-ylmethoxy]phenyl}-4H-1,2,4-triazole-3-thiol with 2-bromopropane.

EXAMPLE LVII

To a stirred solution of 1.33 parts of dimethyl sulfate in 100 parts of dimethylsulfoxide are added 0.32 parts of sodium hydride dispersion 78%. After stirring for one hour at about 50° C., 4.3 parts of cis-4-{4-[2-(2,4-dichlorophenyl)-2-(1H-imidazol-1-ylmethyl)-1,3-dioxolan-4-ylmethoxy]phenyl}-2,4-dihydro-5-methyl-3H-1,2,4-triazol-3-one are added. The whole is stirred for one hour at room temperature. The reaction mixture is poured onto water and the product is extracted twice with trichloromethane. The combined extracts are washed with water, dried, filtered and evaporated. The residue is converted into the nitrate salt in 2-propanol and 1,1'-oxybisethane. The salt is filtered off and crystallized from ethanol, yielding 2.6 parts (53%) of cis-4-{4-[2-(2,4-dichlorophenyl)-2-(1H-imidazol-1-ylmethyl)-1,3-dioxolan-4-ylmethoxy]phenyl}-2,4-dihydro-2,5-dimethyl-3H-1,2,4-triazol-3-one mononitrate; mp. 208 6° C.

EXAMPLE LVIII

To a stirred solution of 1.74 parts of bromoethane and 6 parts of cis-4-{4-[2-(2,4-dichlorophenyl)-2-(1H-imidazol-1-ylmethyl)-1,3-dioxolan-4-ylmethoxy]-phenyl}-2,4-dihydro-3H-1,2,4-triazol-3-one in 100 parts of dimethylsulfoxide are added 0.5 parts of sodium hydride dispersion 78% and the whole is stirred for 2 hours at about 40° C. The reaction mixture is poured onto water and the product is extracted with trichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is crystallized from a mixture of 4-methyl-2-pentanone and 2,2'-oxybispropane. The product is filtered off and dried, yielding 4.1 parts (66%) of cis-4-{4-[2-(2,4-dichlorophenyl)-2-(1H-imidazol-1-ylmethyl)-1,3-dioxolan-4-ylmethoxy]-phenyl}-2-ethyl-2,4-dihydro-3H-1,2,4-triazol-3-one; mp. 112° C.

EXAMPLE LIX

Following the procedure of Example LVIII and using equivalent amounts of the appropriate starting materials there are prepared: cis-4-{4-[2-(2,4-dichlorophenyl)-2-(1H-imidazol-1-ylmethyl)-1,3-dioxolan-4-ylmethoxy]phenyl}-2,4-dihydro-5-methyl-2-(1-methylethyl)-3H-1,2,4-triazol-3-one; m.p. 170.7° C. by the reaction of cis-4-{4-[2-(2,4-dichlorophenyl)-2-(1H-imidazol-1-ylmethyl)-1,3-dioxolan-4-ylmethyl]phenyl}-2,4-dihydro-5-methyl-3H-1,2,4-triazol-3-one with 2-bromopropane; and cis-4-{4-[2-(2,4-dichlorophenyl)-2-(1H-imidazol-1-ylmethyl)-1,3-dioxolan-4-ylmethoxy]-phenyl}-2-ethyl-2,4-dihydro-5-methyl-3H-1,2,4-triazol-3-one; m.p. 154.5° C. by the reaction of cis-4-{4-[2-(2,4-dichlorophenyl)-2-(1H-imidazol-1-ylmethyl)-1,3-dioxolan-4-ylmethoxy]-phenyl}-2,4-dihydro-5-methyl-3H-1,2,4-triazol-3-one with bromoethane.

EXAMPLE LX

A mixture of 1 part of sodium azide, 2 parts of 1,1',1"-[methylidynetris(oxy)]trisethane, 4.2 parts of cis-4-[2-(2,4-dichlorophenyl)-2-(1H-imidazol-1-ylmethyl)-1,3-dioxolan-4-ylmethoxy]benzenamine and 50 parts of acetic acid is stirred and heated for 4 hours at 70° C. The reaction mixture is cooled, poured onto water and neutralized with potassium carbonate. The product is extracted with dichloromethane. The extract is dried, filtered and evaporated. The residue is crystallized from a mixture of 4-methyl-2-pentanone and 2,2'-oxybispropane. The product is filtered off and recrystallized from 4-methyl-2-pentanone, yielding 2.9 parts (61%) of cis-1-{4-[2-(2,4-dichlorophenyl)-2-(1H-imidazol-1-ylmethyl)-1,3-dioxolan-4-ylmethoxy]phenyl}-1H-tetrazole; mp. 132.6° C.

EXAMPLE LXI

A mixture of 1.3 parts of sodium azide, 4.6 parts of cis-1-[2-(2,4-dichlorophenyl)-4-(4-isothiocyanatophenyoxymethyl-1,3-dioxolan-2-ylmethyl]-1H-imidazole and 80 parts of methanol is stirred and refluxed for one hour. Then there is added one part of sodium hydroxide and stirring at reflux is continued for one hour. The reaction mixture is cooled, poured onto water and washed with 1,1'-oxybisethane. The aqueous phase is acidified with hydrochloric acid till pH=4.

The precipitated product is filtered off and crystallized from 1-butanol, yielding 2.8 parts (55%) of cis-1-{4-[2-(2,4-dichlorophenyl)-2-(1H-imidazol-1ylmethyl)-1,3-dioxolan-4-ylmethoxy]phenyl}-1H-tetrazole-5-thiol; mp. 211.7° C.

EXAMPLE LXII

A mixture of 5 parts of ethanimidamide hydrochloride, 5 parts of cis-N-{4-[2-(2,4-dichlorophenyl)-2-(1H-imidazol-1-ylmethyl)-1,3-dioxolan-4-ylmethoxy]-phenyl}hydrazinecarbothioamide, 5 parts of sodium acetate and 60 parts of 1-butanol is stirred and refluxed for 30 minutes. The reaction mixture is cooled, 100 parts of water and 210 parts of 2,2'-oxybispropane are added and the whole is stirred for 30 minutes at room temperature. The precipitated product is filtered off, washed with water and with 2-propanol and crystallized from 1-butanol. The product is filtered off and boiled in 80 parts of methanol. After cooling, it is filtered off again and dried for 2 days at 80° C., yielding 3 parts of cis-4-{4-[2-(2,4-dichlorophenyl)-2-(1H-imidazol-1-ylmethyl)-1,3-dioxolan-4-ylmethoxy]phenyl}-5-methyl-4H-1,2,4-triazole-3-thiol; mp. 247.6° C.

EXAMPLE LXIII

A mixture of 60 parts of cis-1-{4-[2-(2,4-dichlorophenyl)-2-(1H-imidazol-1-ylmethyl)-1,3-dioxolan-4-ylmethoxy]phenyl}-1H-imidazole and 900 parts of ethyl acetate is stirred and heated to reflux till all solid enters solution. After cooling to about 50° C., there are added dropwise 45 parts of 2-propanol, previously saturated with hydrogen chloride. After stirring overnight at room temperature, the formed hydrochloride salt is filtered off and dried in vacuo at 45° C., yielding 57 parts (81%) of cis-1-{4-[2-(2,4-dichlorophenyl)-2-(1H-imidazol-1-ylmethyl)-1,3-dioxolan-4-ylmethoxy]-phenyl}-1H-imidazole dihydrochloride; mp. 238.7° C.

EXAMPLE LXIV

To a stirred mixture of 3.2 parts of 4-(1H-imidazol-1-yl)phenol and 100 parts of dimethylsulfoxide are added 0.7 parts of sodium hydride dispersion 76.5% and the whole is stirred for 30 minutes at room temperature. Then there are added 8.2 parts of cis-[2-(2,4-dichlorophenyl)-2-(1H-1,2,4-triazol-1-ylmethyl)-1,3-dioxolan-4-ylmethyl]methanesulfonate and stirring is continued for 3 hours at 130° C. The reaction mixture is cooled, poured onto water and the product is extracted with dichloromethane. The extract is washed with water, dried, filtered and evaporated. The residue is purified by column-chromatography over silica gel using a mixture of trichloromethane and methanol (97:3 by volume) as eluent. The pure fractions are collected and the eluent is evaporated. The residue is crystallized from 4-methyl-2-pentanone. The product is filtered off and dried, yielding 4.4 parts of cis-1-{2-(2,4-dichlorophenyl)-4-[4-(1H-imidazol-1-yl)-phenoxymethyl]-1,3-dioxolan-2-ylmethyl}-1H-1,2,4-triazole; mp. 128.8° C.

EXAMPLE LXV

Following the procedure of Example LXIV and using equivalent amounts of the appropriate starting materials there are prepared:
cis-1-[2-(2,4-dichlorophenyl)-4-{4 [2-(methylthio)-1H-imidazol-1-yl]phenoxymethyl}-1,3-dioxolan-2-ylmethyl]-1H-1,2,4-triazole; mp. 185.6° C.;
cis-4-{4-[2-(2,4-dichlorophenyl)-2-(1H-1,2,4-triazol-1-ylmethyl)-1,3-dioxolan-4-ylmethoxy]phenyl}-3-(methylthio)-4H-1,2,4-triazole; mp. 184.7° C.; and
cis-1-[2-(2,4-dichlorophenyl)-4-{4-[2-(ethylthio)-1H-imidazol-1-yl]phenoxymethyl}-1,3dioxolan-2-ylmethyl]-1H-1,2,4-triazole dinitrate; mp. 149.6°–150.8° C.

EXAMPLE LXVI

Following the procedure of Example XLVIII and using equivalent amounts of appropriate starting materials the following methanesulfonates are prepared:
[2-(4-methoxyphenyl)-2-(1H-1,2,4-triazol-1-ylmethyl)-1,3-dioxolan-4-ylmethyl] methanesulfonate;
[2-phenyl-2-(1H-1,2,4-triazol-1-ylmethyl)-1,3-dioxolan-4-ylmethyl] methanesulfonate;
[2-(4-chlorophenyl)-2-(1H-1,2,4-triazol-1-ylmethyl)-1,3-dioxolan-4-ylmethyl] methanesulfonate;
[2-(4-bromophenyl)-2-(1H-1,2,4-triazol-1-ylmethyl)-1,3-dioxolan-4-ylmethyl] methanesulfonate;
[2-(4-fluorophenyl)-2-(1H-1,2,4-triazol-1-ylmethyl)-1,3-dioxolan-4-ylmethyl] methanesulfonate;
[2-(4-methylphenyl)-2-(1H-1,2,4-triazol-1-ylmethyl)-1,3-dioxolan-4-ylmethyl] methanesulfonate; and
[2-(4-methoxyphenyl)-2-(1H-1,2,4-triazol-1-ylmethyl)-1,3-dioxolan-4-ylmethyl] methanesulfonate.

EXAMPLE LXVII

Following the procedure of Example VIII and using equivalent amounts of the appropriate starting materials the following compounds of formula (I) are still prepared.
1-{2-(2,4-dichlorophenyl)-4[2-(1H-pyrrol-1-yl)phenoxymethyl]-1,3-dioxolan-2-ylmethyl}-1H-imidazole;
1-{2-(3-chlorophenyl)-4-[4-(1H-pyrrol-1-yl)phenoxymethyl]-1,3-dioxolan-2-ylmethyl}-1H-imidazole;
1-{2-(4-methoxyphenyl)-4-[4-(1H-pyrrol-1-yl)phenoxymethyl]-1,3-dioxolan-2-ylmethyl}-1H-imidazole;
1{2-(4-methylphenyl)-4-[4-(1H-pyrrol-1-yl)phenoxymethyl]-1,3-dioxolan-2-ylmethyl}-1H-imidazole;
1-{2-(2,4-dichlorophenyl)-4-[4-(1H-pyrrol-1-yl)phenoxymethyl]-1,3-dioxolan-2-ylmethyl}-1H-1,2,4-triazole;
1-{2-(2,4-dichlorophenyl)-4-[2-(1H-pyrrol-1-yl)phenoxymethyl]-1,3-dioxolan-2-ylmethyl}-1H-1,2,4-triazole;
1-{2-(4-methoxyphenyl)-4-[4-(1H-pyrrol-1-yl)phenoxymethyl]-1,3-dioxolan-2-ylmethyl}-1H-1,2,4-triazole;
1-{2-(4-methylphenyl)-4-[4-(1H-pyrrol-1-yl)phenoxymethyl]-1,3-dioxolan-2-ylmethyl}-1H-1,2,4-triazole;
1-{3-[2-(2,4-dichlorophenyl)-2-(1H-imidazol-1-ylmethyl)-1,3-dioxolan-4-ylmethoxy]phenyl}-1H-pyrazole;
1-{2-[2-(2,4-dichlorophenyl)-2-(1H-imidazol-1-ylmethyl)-1,3-dioxolan-4-ylmethoxy]phenyl}-1H-pyrazole;
1-{4-[2-(3-chlorophenyl)-2-(1H-imidazol-1ylmethyl)-1,2-dioxolan-4-ylmethoxy]phenyl}-1H-pyrazole;
1-{2-(2,4-dichlorophenyl)-4-[4-(1H-pyrazol-1-yl)phenoxymethyl]-1,3-dioxolan-2-ylmethyl}-1H-1,2,4-triazole;
1-{2-(4-methylphenyl)-4-[4-(1H-pyrazol-1-yl)phenoxymethyl]-1,3-dioxolan-2-ylmethyl}-1H-1,2,4-triazole;
1-{3-[2-(2,4-dichlorophenyl)-2-(1H-imidazol-1-ylmethyl)-1,3-dioxolan-4-ylmethoxy]phenyl}-1H-1,2,4-triazole;
1-{2-[2-(2,4-dichlorophenyl)-2-(1H-imidazol-1-ylmethyl)-1,3-dioxolan-4-ylmethoxy]phenyl}-1H-1,2,4-triazole;
1-{4-[2-(3-chlorophenyl)-2-(1H-imidazol-1-ylmethyl)-1,3-dioxolan-4-ylmethyl]phenyl}-1H-1,2,4-triazole;

1-{4-[2-(1H-imidazol-1-ylmethyl)-2-(4-methylphenyl)-1,3-dioxolan-4-ylmethoxy]phenyl}-1H-1,2,4-triazole;
1-{4-[2-(1H-imidazol-1-ylmethyl)-2-(4-methoxyphenyl)-1,3-dioxolan-4-ylmethoxy]phenyl}-1H-1,2,4-triazole;
1-{2-(2,4-dichlorophenyl)-4-[4-(1H-imidazol-1-yl)phenoxymethyl]-1,3-dioxolan-2-ylmethyl}-1H-1,2,4-triazole;
1-{2-(2,4-dichlorophenyl)-4-[3-(1H-imidazol-1-yl)phenoxymethyl]-1,3-dioxolan-2-ylmethyl}-1H-1,2,4-triazole;
1-{2-(2,4-dichlorophenyl)-4-[2-(1H-imidazol-1-yl)phenoxymethyl]-1,3-dioxolan-2-ylmethyl}-1H-1,2,4-triazole;
1-{4-[4-(1H-imidazol-1-yl)phenoxymethyl]-2-(4-methylphenyl)-1,3-dioxolan-2-ylmethyl}-1H-1,2,4-triazole;
1-{4-[4-(1H-imidazol-1-yl)phenoxymethyl]-2-(4-methoxyphenyl)-1,3-dioxolan-2-ylmethyl}-1H-1,2,4-triazole;
4-{3-[2-(2,4-dichlorophenyl)-2-(1H-imidazol-1-ylmethyl)-1,3-dioxolan-4-ylmethoxy]phenyl}-4H-1,2,4-triazole;
4-{2-[2-(2,4-dichlorophenyl)-2-(1H-imidazol-1-ylmethyl)-1,3-dioxolan-4-ylmethoxy]phenyl}-4H-1,2,4-triazole;
4-{4-[2-(1H-imidazol-1-ylmethyl)-2-(4-methylphenyl)-1,3-dioxolan-4-ylmethoxy]phenyl}-4H-1,2,4-triazole;
4-{4-[2-(1H-imidazol-1-ylmethyl)-2-(4-methoxyphenyl)-1,3-dioxolan-4-ylmethoxy]phenyl}-4H-1,2,4-triazole;
1-{2-(2,4-dichlorophenyl)-4-[2-(4H-1,2,4-triazol-4-yl)phenoxymethyl]-1,3-dioxolan-2-ylmethyl}-1H-1,2,4-triazole;
1-{2-(4-methylphenyl)-4-[4-(4H-1,2,4-triazol-4-yl)phenoxymethyl]-1,3-dioxolan-2ylmethyl}-1H-1,2,4-triazole; and
1-{2-(4-methoxyphenyl)-4-[4-(4H-1,2,4-triazol-4-yl)phenoxymethyl]-1,3-dioxolan-2-ylmethyl}-1H-1,2,4-triazole.

EXAMPLE LXVIII

Following the procedure of Example V and using equivalent amounts of the appropriate starting materials there are prepared:
3-[2-(2,4-dichlorophenyl)-2-(1H-imidazol-1-ylmethyl)-1,3-dioxolan-4-ylmethoxy]benzenamine; 2-[2-(2,4-dichlorophenyl)-2-(1H-imidazol-1-ylmethyl)-1,3-dioxolane-4-ylmethoxy]benzenamine;
4-[2-(2,4-dichlorophenyl)-2-(1H-1,2,4-triazol-1-ylmethyl)-1,3-dioxolan-4-ylmethoxy]benzenamine;
4-[2-(1H-imidazol-1-ylmethyl)-2-(4-methylphenyl)-1,3-dioxolan-4-ylmethoxy]benzenamine; and
4-[2-(1H-imidazol-1-ylmethyl)-2-(4-methoxyphenyl)-1,3-dioxolan-4-ylmethoxy]benzenamine.

EXAMPLE LXIX

Following the procedure of Example LX and using equivalent amounts of the appropriate starting materials there are prepared:
1-{3-[2-(2,4-dichlorophenyl)-2-(1H-imidazol-1-ylmethyl)-1,3-dioxolan-4-ylmethoxy]phenyl}-1-H-tetrazole;
1-{2-[2-(2,4-dichlorophenyl)-2-(1H-imidazol-1-ylmethyl)-1,3-dioxolan-4-ylmethoxy]phenyl}-1H-tetrazole;
1-{4-[2-(2,4-dichlorophenyl)-2-(1H-1,2,4-triazol-1-ylmethyl)-1,3-dioxolan-4-ylmethoxy]phenyl}-1H-tetrazole;
1-{4-[2-(1H-imidazol-1-ylmethyl)-2-(4-methylphenyl)-1,3-dioxolan-4-ylmethoxy]phenyl}-1H-tetrazole; and
1-{4-[2-(1H-imidazol-1-ylmethyl)-2-(4-methoxyphenyl)-1,3-dioxolan-4-ylmethyl]phenyl}-1H-tetrazole.

EXAMPLE LXX

Following the procedure of Example VI and using equivalent amounts of the appropriate starting materials there are prepared:
N-{3-[2-(2,4-dichlorophenyl)-2-(1H-imidazol-1-ylmethyl)-1,3-dioxolan-4-ylmethoxy]phenyl}hydrazinecarboxamide;
N-{4-[2-(2,4-dichlorophenyl)-2-(1H-1,2,4-triazol-1-ylmethyl)-1,3-dioxolan-4-ylmethoxy]phenyl}hydrazinecarboxamide;
N-{4-[2-(1H-imidazol-1-ylmethyl)-2-(4-methylphenyl)-1,3-dioxolan-4-ylmethoxy]phenyl}hydrazinecarboxamide; and
N-{4-[2-(1H-imidazol-1-ylmethyl)-2-(4-methoxyphenyl)-1,3-dioxolan-4-ylmethoxy]phenyl}hydrazinecarboxamide.

EXAMPLE LXXI

Following the procedure of Example XIV and using equivalent amounts of the appropriate starting materials there are prepared:
4-{3-[2-(2,4-dichlorophenyl)-2-(1H-imidazol-1-ylmethyl)-1,3-dioxolan-4-ylmethoxy]phenyl}-2,4-dihydro-3H-1,2,4-triazol-3-one;
4-{4-[2-(2,4-dichlorophenyl)-2-(1H-1,2,4-triazol-1-ylmethyl)-1,3-dioxolan-4-ylmethoxy[phenyl}-2,4-dihydro-3H-1,2,4-triazol-3-one; 4-{4-[2-(1H-imidazol-1-ylmethyl)-2-(4-methylphenyl)-1,3-dioxolan-4-ylmethoxy]phenyl}-2,4-dihydro-3H-1,2,4-triazol-3-one; and
4-{4-[2-(1H-imidazol-1-ylmethyl)-2-(4-methoxyphenyl)-1,3-dioxolan-4-ylmethoxy]phenyl}-2,4-dihydro-3H-1,2,4-triazol-3-one.

EXAMPLE LXXII

Following the procedure of the first step of Example VII and using equivalent amounts of the appropriate starting materials there are prepared:
1-[2-(2,4-dichlorophenyl)-4-(3-isothiocyanatophenoxymethyl)-1,3-dioxolan-2-ylmethyl]-1H-imidazole;
1-[2-(2,4-dichlorophenyl)-4-(4-isothiocyanatophenoxymethyl)-1,3-dioxolan-2-ylmethyl]-1H-1,2,4-triazole;
1-[4-(4-isothiocyanatophenoxymethyl)-2-(4-methylphenyl)-1,3-dioxolan-2-ylmethyl]-1H-imidazole; and
1-[4-(4-isothiocyanatophenoxymethyl)-2-(4-methoxyphenyl)-1,3-dioxolan-2-ylmethyl]-1H-imidazole.

EXAMPLE LXXIII

Following the procedure of Example LXI and using equivalent amounts of the appropriate starting materials there are prepared:
1-{3-[2-(2,4-dichlorophenyl)-2-(1H-imidazol-1-ylmethyl)-1,3-dioxolan-4-ylmethoxy]phenyl}-1H-tetrazole-5-thiol; 1-{4-[2-(2,4-dichlorophenyl)-2-(1H-1,2,4-triazol-1-ylmethyl)-1,3-dioxolan-4-ylmethoxy]phenyl}-1H-tetrazole-5-thiol;
1-{4-[2-(1H-imidazol-1-ylmethyl)-2-(4-methylphenyl)-1,3-dioxolan-4-ylmethoxy]phenyl}-1H-tetrazole-5-thiol; and
1-{4-[2-(1H-imidazol-1-ylmethyl)-2-(4-methoxyphenyl)-1,3-dioxolan-4-ylmethoxy]phenyl}-1H-tetrazole-5-thiol.

EXAMPLE LXXIV

Following the procedure of the second step of Example VII and using equivalent amounts of the appropriate starting materials there are prepared:

N-{3-[2-(2,4-dichlorophenyl)-2-(1H-imidazol-1-ylmethyl)-1,3-dioxolan-4-ylmethoxy]phenyl}hydrazinecarbothioamide;

N-{4-[2-(2,4-dichlorophenyl)-2-(1H-1,2,4-triazol-1-ylmethyl)-1,3-dioxolan-4-ylmethoxy]phenyl}hydrazinecarbothioamide;

N-{4-[2-(1H-imidazol-1-ylmethyl)-2-(4-methylphenyl)-1,3-dioxolan-4-ylmethoxy]phenyl}hydrazinecarbothioamide; and N-{4-[2-(1H-imidazol-1-ylmethyl)-2-(4-methoxyphenyl)-1,3-dioxolan-4-ylmethoxy]phenyl}hydrazinecarbothioamide.

EXAMPLE LXXV

Following the procedure of Example XVII and using equivalent amounts of the appropriate starting materials there are prepared: 4-{3-[2-(2,4-dichlorophenyl)-2-(1H-imidazol-1-ylmethyl)-1,3-dioxolan-4-ylmethoxy]phenyl}-4H-1,2,4-triazole-3-thiol;

4-{4-[2-(2,4-dichlorophenyl)-2-(1H-1,2,4-triazol-1-ylmethyl)-1,3-dioxolan-4-ylmethoxy]phenyl}-4H-1,2,4-triazole-3-thiol;

4-{4-[2-(1H-imidazol-1-ylmethyl)-2-(4-methylphenyl)-1,3-dioxolan-4-ylmethoxy]phenyl}-4H-1,2,4-triazole-3-thiol; and 4-{4-[2-(1H-imidazol-1-ylmethyl)-2-(4-methoxyphenyl)-1,3-dioxolan-4-ylmethoxy]phenyl}-4H-1,2,4-triazole-3-thiol.

EXAMPLE LXXVI

A mixture of 17 parts of (4-methoxyphenyl)hydrazine hydrochloride, 14 parts of 4,4-dimethoxy-2-butanone, 14 parts of potassium carbonate and 240 parts of ethanol is stirred and refluxed for 2 hours. The reaction mixture is evaporated and the residue is stirred and refluxed for 1 hour with 200 parts of a hydrochloric acid solution 10%. The solvent is evaporated and the residue is neutralized with ammonium hydroxide. The product is extracted three times with 2,2'-oxybispropane. The combined extracts are washed with water, dried, filtered and evaporated. The residue is purified by column-chromatography over silica gel using trichloromethane as eluent. The pure fractions are collected and the eluent is evaporated. The residue is crystallized from hexane. The product is filtered off and dried, yielding 2.4 parts of 1-(4-methoxyphenyl)-3-methyl-1H-pyrazole.

EXAMPLE LXXVII

Following the procedure of Example LXIV and using equivalent amounts of the appropriate starting materials there is prepared:

cis-1-{2-(2,4-dichlorophenyl)-4-[4-(3-methyl-1H-pyrazol-1-yl)- phenoxymethyl]-1,3-dioxolan-2-ylmethyl}1H-1,2,4-triazole; mp. 148.6° C.

We claim:

1. A chemical compound selected from the group consisting of an azole derivative having the formula:

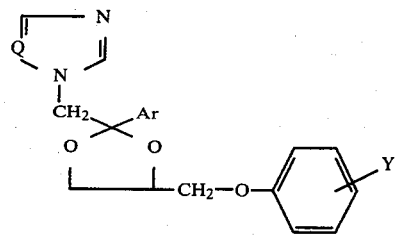

and the pharmaceutically acceptable acid addition salts and stereochemically isomeric forms thereof, wherein:

Q is N;

Ar is a member selected from the group consisting of phenyl and substituted phenyl, said substituted phenyl having from 1 to 3 substituents independently selected from the group consisting of halo, lower alkyl and lower alkyloxy; and the radical Y is a member selected from the group consisting of:

a 1H-1,2,4-triazol-1-yl radical of the formula

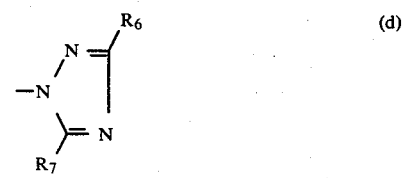

wherein $R_6$ is selected from the group consisting of hydrogen and lower alkylthio, and, $R_7$ is selected from the group consisting of hydrogen, lower alkyl and phenyl;

a 4H-1,2,4-triazol-4-yl radical of the formula

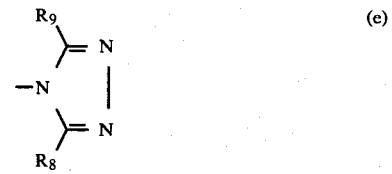

wherein $R_8$ is selected from the group consisting of hydrogen, lower alkyl, lower alkyloxy, lower alkylthio, lower alkylsulfinyl and lower alkylsulfonyl, and, $R_9$ is selected from the group consisting of hydrogen and lower alkyl;

a 2,3-dihydro-4H-1,2,4-triazol-4-yl radical of the formula

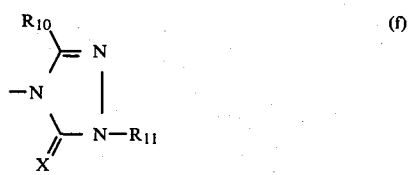

wherein X is selected from the group consisting of O and S, and, $R_{10}$ and $R_{11}$ are each independently selected from the group consisting of hydrogen and lower alkyl, provided that when said X is S then said $R_{11}$ is hydrogen;

a 1H-1,2,3,4-tetrazol-1-yl radical of the formula

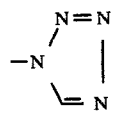

and a 4,5-dihydro-5-thioxo-1H-1,2,3,4-tetrazol-1-yl radical of the formula

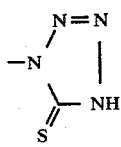

2. A chemical compound selected from the group consisting of cis-4-{4-[2-(2,4-dichlorophenyl)-2-(1H-1,2,4-triazol-1-ylmethyl)-1,3-dioxolan-4-ylmethoxy]-phenyl}-3-(methylthio)-4H-1,2,4-triazole and the pharmaceutically acceptable acid addition salts thereof.

3. A composition for combatting the growth of a microorganism selected from the group consisting of fungus and bacterium comprising an inert carrier material and as an active ingredient an effective amount of a compound selected from the group consisting of an azole derivative having the formula:

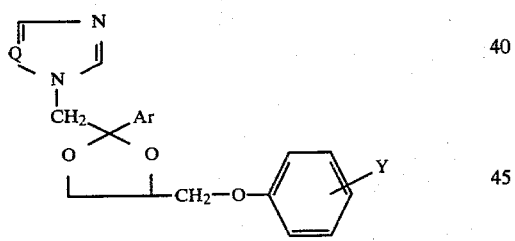

and the pharmaceutically acceptable acid addition salts and stereochemically isomeric forms thereof, wherein:

Q is N;

Ar is a member selected from the group consisting of phenyl and substituted phenyl, said substituted phenyl having from 1 to 3 substituents independently selected from the group consisting of halo, lower alkyl and lower alkyloxy; and the radical Y is a member selected from the group consisting of:

a 1H-1,2,4-triazol-1-yl radical of the formula

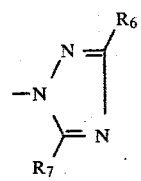

wherein $R_6$ is selected from the group consisting of hydrogen and lower alkylthio, and, $R_7$ is selected from the group consisting of hydrogen, lower alkyl and phenyl;

a 4H-1,2,4-triazol-4-yl radical of the formula

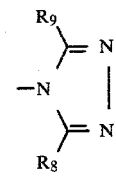

wherein $R_8$ is selected from the group consisting of hydrogen lower alkyl, lower alkyloxy, lower alkylthio, lower alkylsulfinyl and lower alkylsulfonyl, and, $R_9$ is selected from the group consisting of hydrogen and lower alkyl;

a 2,3-dihydro-4H-1,2,4-triazol-4-yl radical of the formula

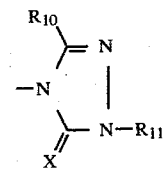

wherein X is selected from the group consisting of O and S, and, $R_{10}$ and $R_{11}$ are each independently selected from the group consisting of hydrogen and lower alkyl, provided that when said X is S then said $R_{11}$ is hydrogen;

a 1H-1,2,3,4-tetrazol-1-yl radical of the formula

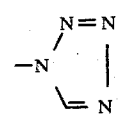

and a 4,5-dihydro-5-thioxo-1H-1,2,3,4-tetrazol-1-yl radical of the formula

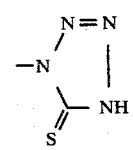

* * * * *